US005856456A

United States Patent [19]
Whitlow et al.

[11] Patent Number: 5,856,456
[45] Date of Patent: Jan. 5, 1999

[54] LINKER FOR LINKED FUSION POLYPEPTIDES

[75] Inventors: Marc D. Whitlow, Princeton; David R. Filpula, Piscataway, both of N.J.

[73] Assignee: Enzon, Inc., Piscataway, N.J.

[21] Appl. No.: 224,591

[22] Filed: Apr. 7, 1994

Related U.S. Application Data

[63] Continuation-in-part of Ser. No. 2,845, Jan. 15, 1993, abandoned, which is a continuation-in-part of Ser. No. 980,529, Nov. 20, 1992, abandoned.

[51] Int. Cl.$^6$ .......................... C12N 15/11; C12N 15/62; C12N 15/13; C07H 21/04
[52] U.S. Cl. .................... 536/23.4; 536/23.5; 536/23.53; 536/24.2; 514/44; 424/135.1; 424/134.1; 424/192.1; 424/194.1; 435/328; 435/320.1; 930/310; 530/387.3
[58] Field of Search ............................... 536/24.2, 23.53, 536/24.4, 23.5; 424/135.1, 134.1, 192.1, 194.1; 514/44; 930/310; 530/387.3

[56] References Cited

U.S. PATENT DOCUMENTS

| | | | |
|---|---|---|---|
| 4,704,692 | 11/1987 | Ladner | 364/496 |
| 4,853,871 | 8/1989 | Pantoliano et al. | 364/496 |
| 4,881,175 | 11/1989 | Ladner | 364/496 |
| 4,908,773 | 3/1990 | Pantoliano et al. | 364/496 |
| 4,939,666 | 7/1990 | Hardman | 364/496 |
| 4,946,778 | 8/1990 | Ladner et al. | 435/69.6 |
| 5,160,723 | 11/1992 | Welt et al. | 424/1.1 |
| 5,258,498 | 11/1993 | Huston et al. | 530/350 |
| 5,534,254 | 7/1996 | Huston et al. | 424/135.1 |

FOREIGN PATENT DOCUMENTS

WO 92/15682  9/1992  WIPO.

OTHER PUBLICATIONS

Whitlow, M. et al., "Multivalent Fvs: characterization of single–chain Fv oligomers and preparation of a bispecific Fv," *Prot. Engin.* 7(8):1017–1026 (Aug. 1994).
Batra et al., "Anti–Tac(Fv)–PE40, a Single Chain Antibody Pseudomonas Fusion Protein Direction at Interleukin 2 Receptor Bearing Cells," *J. Biol. Chem.* 265(25) :15198–15202 (Sep. 5, 1990).
Bedzyk et al., "Immunological and Structural Characterization of a High Affinity Anti–fluorescein Single–Chain Antibody," *J. Biol. Chem.* 265(30) :18615–18620.
Bird et al., "Single–Chain Antigen–Binding Proteins," *Science* 242:423–426 (Oct. 21, 1988).
Breitling et al., "A Surface Expression Vector for Antibody Screening," *Gene* 104:147–153 (1991).
Chaudhary et al., "A Recombinant Immunotoxin Consisting of Two Antibody Variable Domains Fused to Pseudomonas Exotoxin," *Nature* 339:394–397 (Jun. 1, 1989).
Clements, J., "Construction of a Nontoxic Fusion Peptide for Immunization against *E. coli* Strains That Produce Heat–Labile and Heat–Stable Enterotoxins," *Infection and Immunity* 58(5) :1159–1166 (May 1990).
Colcher et al., "In Vivo Tumor Targeting of a Recombinant Single–Chain Antigen–Binding Protein," *J. National Cancer Institute* 82 (14) :1191–1197 (Jul. 18, 1990).
Condra et al., "Bacterial Expression of Antibody Fragments That Block Human Rhinovirus Infection of Cultured Cells," *J. Biol. Chem.* 265(4) :2292–2295 (Feb. 5, 1990).
Essig et al., "Crystallization of Single–Chain Fv Proteins," *J. Mol. Biol.* 234:897–901 (1993).
Fuchs et al., "Targeting Recombinant Antibodies To The Surface of *E. coli:* Fusion To A Peptidoglycan Associated Lipoprotein," *Bio/Technol.* 9:1369–1372 (Dec. 1991).
Harris and Emery, "Therapeutic Antibodies — The Coming of Age," *TiBTech* 11:42–44 (Feb. 1993).
Hird et al., "Immunotherapy with Monoclonal Antibodies" in: Genes and Cancer, eds. Carney et al., John Wiley & Sons Ltd., pp. 183–189 (1990).
Holvoet et al., "Characterization of a Chimeric Plasminogen Activator Consisting of a Single–Chain Fv Fragment Derived from a Fibrin Fragment D–Dimer–specific Antibody and a Truncated Single–Chain Urokinase," *J. Biol. Chem.* 266 (29) :19717–19724 (Oct. 15, 1991).
Huston et al., "Medical Applications of Single–Chain Antibodies," *Int. Rev. Immunol* 10(2–3) :195–217 (1993).
Huston et al., "Protein Engineering of Single–Chain Fv Analogs and Fusion Proteins," *Meth. in Enzymology* 203:46–88 (1991).
Kim et al., "Redesigning a Sweet Protein: Increased Stability and Renaturability," *Protein Eng.* 2(8) :571–575 (1989).
Laroche et al., "Characterization of a Recombinant Single–chain Molecular Comprising the Variable Domains of a Monoclonal Antibody Specific for Human Fibrin Fragment D–Dimer," *J. Biol. Chem.* 266(25) :16343–16349 (Sep. 5, 1991).
Lehninger, A.L., *Principles of Biochemistry*, Worth Publishers, Inc., NY, NY, pp. 150–155 (1982).

(List continued on next page.)

*Primary Examiner*—Lila Feisee
*Assistant Examiner*—John Lucas
*Attorney, Agent, or Firm*—Sterne, Kessler, Goldstein & Fox P.L.L.C.

[57] ABSTRACT

The invention is directed to a novel peptide linker useful for connecting polypeptide constituents into a novel linked fusion polypeptide. The peptide linker of the invention provides greater stability and is less susceptible to aggregation than previously known peptide linkers. The peptide linker of the invention may be up to about 50 amino acids in length and contains at least one occurrence of a charged amino acid followed by a proline. When used for making a single chain Fv (sFv), the peptide linker is preferably from 18 to about 30 amino acids in length. A preferred embodiment of the peptide linker of the invention comprises the sequence:

GSTSGSGXPGSGEGSTKG (SEQ. ID NO 1), where X is a charged amino acid, preferably lysine or arginine. Methods of making linked fusion polypeptides using the peptide linker of the invention are claimed. DNA molecules encoding such linked fusion polypeptides, and methods of producing such linked fusion polypeptides from these DNA molecules are also claimed.

86 Claims, 14 Drawing Sheets

OTHER PUBLICATIONS

Milenic et al., "Construction, Binding Properties, Metabolism, and Tumor Targeting of a Single–Chain Fv Derived from the Pancarcinoma Monoclonal Antibody CC49," *Cancer Research* 51:6363–6371 (Dec. 1991).

Mottez et al., "A Single–Chain Murine Class I Major Transplantation Antigen," *Eur. J. Immunol.* 21:467–471 (1991).

Novotny et al., "A Soluble, Single–Chain T–cell Receptor Fragment Endowed With Antigen–Combining Properties," *Proc. Natl. Acad. Sci. USA* 88:8646–8650 (1991).

Pantoliano et al., "Conformational Stability, Folding, and Ligand–Binding Affinity of Single–Chain Fv Immunoglobulin Fragments Expressed in *E. coli*," *Biochemistry* 30 (42) :10117–10125 (1991).

Schlom, J., "Monoclonal Antibodies: They're More and Less Than You Think" in : Molecular Foundations of Oncology, ed. S. Broder, Publ. Williams & Wilkins, Baltimore, MD, pp. 95–134 (1991).

Scientific Report — Ludwig Institute for Cancer Research — 1991 Annual Scientific Report, Published Apr. 30, 1992.

Seehaus et al., "A Vector for the Removal of Deletion Mutants from Antibody Libraries," *Gene* 114:235–237 (1992).

Soo Hoo et al., "Characterization of a Single–Chain T–cell Receptor Expressed in *E. coli*," *Proc. Natl. Acad. Sci. USA* 89:4759–4763 (May 1992).

Takkinen et al., "An Active Single–Chain Antibody Containing a Cellulase Linker Domain Is Secreted by *E. coli*," *Protein Eng.* 4(7) :837–841 (1991).

Traunecker et al., "Bispecific Single–Chain Molecules (Janusins) Target Cytotoxic Lymphocytes on HIV Infected Cells," *EMBO J.* 10(12) :3655–3659 (1991).

Waldmann, T., "Monoclonal Antibodies in Diagnosis and Therapy," *Science* 252:1657–1661 (Jun. 1991).

Welt et al., "Quantitative Analysis of Antibody Localization in Human Metastatic Colon Cancer: A Phase I Study of Monoclonal Antibody A33," *J. Clinical Oncology* 8(11) :1894–1906 (Nov. 1990).

Whitlow et al., "An Improved Linker for Single–Chain Fv with Reduced Aggregation and Enhanced Proteolytic Stability," *Protein Eng.* 6(8) :989–995 (1993).

Whitlow et al., "Single Chain Fvs," in: Tumor Immunology: A Practical Approach, Publ. by Oxford University Press, pp. 279–291 (1993).

Wootton et al., "The Q–Linker: A Class of Interdomain Sequences Found in Bacterial Multidomain Regulatory Proteins," *Protein Eng.* 2(7) :535–543 (1989).

Yokota et al., "Rapid Tumor Penetration of a Single–Chain Fv and Comparison with Other Immunoglobulin Forms," *Cancer Res.* 52:3402–3408 (Jun. 15, 1992).

4-4-20 V_L / 217 / CC49 V_H gene

```
4-4-20 V_L                          10                                              20
Asp Val Val Met Thr Gln Thr Pro Leu Ser Leu Pro Val Ser Leu Gly Asp Gln Ala Ser
GAC GTC GTT ATG ACT CAG ACA CCA CTA TCA CTT CCT GTT AGT CTA GGT GAT CAA GCC TCC
Aat II
                                    30                                              40
Ile Ser Cys Arg Ser Ser Gln Ser Leu Val His Ser Asn Gly Asn Thr Tyr Leu Arg Trp
ATC TCT TGC AGA TCT AGT CAG AGC CTT GTA CAC AGT AAT GGA AAC ACC TAT TTA CGT TGG 50                                              60
Tyr Leu Gln Lys Pro Gly Gln Ser Pro Lys Val Leu Ile Tyr Lys Val Ser Asn Arg Phe
TAC CTG CAG AAG CCA GGC CAG TCT CCA AAG GTC CTG ATC TAC AAA GTT TCC AAC CGA TTT 70                                              80
Ser Gly Val Pro Asp Arg Phe Ser Gly Ser Gly Ser Gly Thr Asp Phe Thr Leu Lys Ile
TCT GGG GTC CCA GAC AGG TTC AGT GGC AGT GGA TCA GGG ACA GAT TTC ACA CTC AAG ATC 90                                             100
Ser Arg Val Glu Ala Glu Asp Leu Gly Val Tyr Phe Cys Ser Gln Ser Thr His Val Pro
AGC AGA GTG GAG GCT GAG GAT CTG GGA GTT TAT TTC TGC TCT CAA AGT ACA CAT GTT CCG 110          217 Linker                        120
Trp Thr Phe Gly Gly Gly Thr Lys Leu Glu Ile Lys Gly Ser Thr Ser Gly Lys Pro Ser
TGG ACG TTC GGT GGA GGC ACC AAG CTT GAA ATC AAA GGT TCT ACC TCT GGT AAA CCA TCT
                                       Hind III
           CC49 V_H                 130                                             140
Glu Gly Lys Gly Gln Val Gln Leu Gln Gln Ser Asp Ala Glu Leu Val Lys Pro Gly Ala
GAA GGC AAA GGT CAG GTT CAG CTG CAG CAG TCT GAC GCT GAG TTG GTG AAA CCT GGG GCT
                                     Pvu II PstI
                                    150                                            160
Ser Val Lys Ile Ser Cys Lys Ala Ser Gly Tyr Thr Phe Thr Asp His Ala Ile His Trp
TCA GTG AAG ATT TCC TGC AAG GCT TCT GGC TAC ACC TTC ACT GAC CAT GCA ATT CAC TGG 170                                            180
Val Lys Gln Asn Pro Glu Gln Gly Leu Glu Trp Ile Gly Tyr Phe Ser Pro Gly Asn Asp
GTG AAA CAG AAC CCT GAA CAG GGC CTG GAA TGG ATT GGA TAT TTT TCT CCC GGA AAT GAT 190                                            200
Asp Phe Lys Tyr Asn Glu Arg Phe Lys Gly Lys Ala Thr Leu Thr Ala Asp Lys Ser Ser
GAT TTT AAA TAC AAT GAG AGG TTC AAG GGC AAG GCC ACA CTG ACT GCA GAC AAA TCC TCC 210                                            220
Ser Thr Ala Tyr Val Gln Leu Asn Ser Leu Thr Ser Glu Asp Ser Ala Val Tyr Phe Cys
AGC ACT GCC TAC GTG CAG CTC AAC AGC CTG ACA TCT GAG GAT TCT GCA GTG TAT TTC TGT 230                                            240
Thr Arg Ser Leu Asn Met Ala Tyr Trp Gly Gln Gly Thr Ser Val Thr Val Ser
ACA AGA TCC CTG AAT ATG GCC TAC TGG GGT CAA GGA ACC TCA GTC ACC GTC TCC TAA TAG
Asp
GAT CC
Bam HI
```

FIG.3

CC49 V_L / 217 / 4-4-20 V_H gene

CC49 V_L

```
                                    10                                      20
Asp Val Val Met Ser Gln Ser Pro Ser Ser Leu Pro Val Ser Val Gly Glu Lys Val Thr
GAC GTC GTG ATG TCA CAG TCT CCA TCC TCC CTA CCT GTG TCA GTT GGC GAG AAG GTT ACT
Aat II
                                    30                                      40
Leu Ser Cys Lys Ser Ser Gln Ser Leu Leu Tyr Ser Gly Asn Gln Lys Asn Tyr Leu Ala
TTG AGC TGC AAG TCC AGT CAG AGC CTT TTA TAT AGT GGT AAT CAA AAG AAC TAC TTG GCC
                                    50                                      60
Trp Tyr Gln Gln Lys Pro Gly Gln Ser Pro Lys Leu Leu Ile Tyr Trp Ala Ser Ala Arg
TGG TAC CAG CAG AAA CCA GGG CAG TCT CCT AAA CTG CTG ATT TAC TGG GCA TCC GCT AGG
                                    70                                      80
Glu Ser Gly Val Pro Asp Arg Phe Thr Gly Ser Gly Ser Gly Thr Asp Phe Thr Leu Ser
GAA TCT GGG GTC CCT GAT CGC TTC ACA GGC AGT GGA TCT GGG ACA GAT TTC ACT CTC TCC
                                    90                                      100
Ile Ser Ser Val Lys Thr Glu Asp Leu Ala Val Tyr Tyr Cys Gln Gln Tyr Tyr Ser Tyr
ATC AGC AGT GTG AAG ACT GAA GAC CTG GCA GTT TAT TAC TGT CAG CAG TAT TAT AGC TAT
                                   110            217 Linker                120
Pro Leu Thr Phe Gly Ala Gly Thr Lys Leu Val Leu Lys Gly Ser Thr Ser Gly Lys Pro
CCC CTC ACG TTC GGT GCT GGG ACC AAG CTT GTG CTG AAA GGC TCT ACT TCC GGT AAA CCA
                                   Hind III
            4-4-20 V_H        140
Ser Glu Gly Lys Gly Glu Val Lys Leu Asp Glu Thr Gly Gly Gly Leu Val Gln Pro Gly
TCT GAA GGT AAA GGT GAA GTT AAA CTG GAT GAG ACT GGA GGA GGC TTG GTG CAA CCT GGG
                                   150                                      160
Arg Pro Met Lys Leu Ser Cys Val Ala Ser Gly Phe Thr Phe Ser Asp Tyr Trp Met Asn
AGG CCC ATG AAA CTC TCC TGT GTT GCC TCT GGA TTC ACT TTT AGT GAC TAC TGG ATG AAC
                                   170                                      180
Trp Val Arg Gln Ser Pro Glu Lys Gly Leu Glu Trp Val Ala Gln Ile Arg Asn Lys Pro
TGG GTC CGC CAG TCT CCA GAG AAA GGA CTG GAG TGG GTA GCA CAA ATT AGA AAC AAA CCT
                                   190                                      200
Tyr Asn Tyr Glu Thr Tyr Tyr Ser Asp Ser Val Lys Gly Arg Phe Thr Ile Ser Arg Asp
TAT AAT TAT GAA ACA TAT TAT TCA GAT TCT GTG AAA GGC AGA TTC ACC ATC TCA AGA GAT
                                   210                                      220
Asp Ser Lys Ser Ser Val Tyr Leu Gln Met Asn Asn Leu Arg Val Glu Asp Met Gly Ile
GAT TCC AAA AGT AGT GTC TAC CTG CAA ATG AAC AAC TTA AGA GTT GAA GAC ATG GGT ATC
                                   230                                      240
Tyr Tyr Cys Thr Gly Ser Tyr Tyr Gly Met Asp Tyr Trp Gly Gln Gly Thr Ser Val Thr
TAT TAC TGT ACG GGT TCT TAC TAT GGT ATG GAC TAC TGG GGT CAA GGA ACC TCA GTC ACC
Val Ser
GTC TCC TAA TAA GGA TCC
              Bam HI
```

FIG. 4

Analysis: Channel A

| Peak No. | Time | Type | Height(μV) | Area(μV-sec) | Area% |
|---|---|---|---|---|---|
| 1 | 17.090 | N1 | 1651 | 348239 | 0.778 |
| 2 | 18.940 | N2 | 8014 | 669441 | 1.496 |
| 3 | 21.775 | N3 | 104401 | 8617252 | 19.263 |
| 4 | 30.100 | N4 | 74925 | 9753616 | 21.804 |
| 5 | 33.455 | N5 | 106864 | 15749605 | 35.208 |
| 6 | 38.940 | N6 | 17296 | 2833701 | 6.334 |
| 7 | 42.010 | N7 | 12645 | 1637917 | 3.661 |
| 8 | 44.640 | N8 | 9287 | 1968584 | 4.400 |
| 9 | 57.055 | N9 | 13767 | 2012338 | 4.498 |
| 10 | 57.610 | N10 | 9323 | 210914 | 0.471 |
| 11 | 58.240 | X11 | 6824 | 930855 | 2.080 |
| Total Area | | | | 44732462 | 99.993 |

A33/212 Single-chain Fv

A33 V$_L$

```
                                        10                                           20
Asp Val Val Met Thr Gln Ser Gln Lys Phe Met Ser Thr Ser Val Gly Asp Arg Val Ser
GAC GTC GTG ATG ACC CAG TCT CAA AAA TTC ATG TCC ACA TCA GTA GGA GAC AGG GTC AGC
Aat II
                                        30                                           40
Ile Thr Cys Lys Ala Ser Gln Asn Val Arg Thr Val Val Ala Trp Tyr Gln Gln Lys Pro
ATC ACC TGC AAG GCC AGT CAG AAT GTT CGT ACT GTT GTA GCC TGG TAT CAA CAG AAA CCA
                                        50                                           60
Gly Gln Ser Pro Lys Thr Leu Ile Tyr Leu Ala Ser Asn Arg His Thr Gly Val Pro Asp
GGG CAG TCT CCT AAA ACA CTG ATT TAC TTG GCC TCC AAC CGG CAC ACT GGA GTC CCT GAT
                                        70                                           80
Arg Phe Thr Gly Ser Gly Ser Gly Thr Asp Phe Thr Leu Thr Ile Ser Asn Val Gln Ser
CGC TTC ACA GGC AGT GGA TCT GGG ACA GAT TTC ACT CTC ACC ATT AGC AAT GTG CAA TCT
                                        90                                          100
Glu Asp Leu Ala Asp Tyr Phe Cys Leu Gln His Trp Ser Tyr Pro Leu Thr Phe Gly Ser
GAA GAC CTG GCA GAT TAT TTC TGT CTG CAA CAT TGG AGT TAT CCT CTC ACG TTC GGA TCC
                                                                                Bam HI
                            212 Linker                                              120
Gly Thr Lys Leu Glu Val Lys Gly Ser Thr Ser Gly Ser Gly Lys Ser Ser Glu Gly Lys
GGG ACA AAG TTG GAA GTA AAA GGT TCT ACC TCT GGT TCT GGT AAA TCT TCT GAA GGT AAA A33 V$_H$                         130                                          140
Gly Glu Val Lys Leu Val Glu Ser Gly Gly Gly Leu Val Lys Pro Gly Gly Ser Leu Lys
GGT GAA GTG AAG CTT GTG GAG TCT GGG GGA GGC TTA GTG AAG CCT GGA GGG TCC CTG AAA
                Hind III
                                        150                                          160
Leu Ser Cys Ala Ala Ser Gly Phe Ala Phe Ser Thr Tyr Asp Met Ser Trp Val Arg Gln
CTC TCC TGT GCA GCC TCT GGA TTC GCT TTC AGT ACC TAT GAC ATG TCT TGG GTT CGC CAG
                                        170                                          180
Thr Pro Glu Lys Arg Leu Glu Trp Val Ala Thr Ile Ser Ser Gly Gly Ser Tyr Thr Tyr
ACT CCG GAG AAG AGG CTG GAG TGG GTC GCA ACC ATT AGT AGT GGT GGT AGT TAC ACC TAC
                                        190                                          200
Tyr Leu Asp Ser Val Lys Gly Arg Phe Thr Ile Ser Arg Asp Ser Ala Arg Asn Thr Leu
TAT TTA GAC AGT GTG AAG GGC CGA TTC ACC ATC TCC AGA GAC AGT GCC AGG AAC ACC CTA
                                        210                                          220
Tyr Leu Gln Met Ser Ser Leu Arg Ser Glu Asp Thr Ala Leu Tyr Tyr Cys Ala Pro Thr
TAC CTG CAA ATG AGC AGT CTG AGG TCT GAG GAC ACG GCC TTG TAT TAC TGT GCA CCG ACT
                                        230                                          240
Thr Val Val Pro Phe Ala Tyr Trp Gly Gln Gly Thr Leu Val Thr Val Ser
ACG GTA GTC CCG TTT GCT TAC TGG GGC CAA GGG ACT CTG GTC ACT GTC TCT TAA
TAG ATCT
Bgl II
```

FIG. 12

A33/218 Single-chain Fv

A33 V$_L$

```
                                    10                                      20
Asp Val Val Met Thr Gln Ser Gln Lys Phe Met Ser Thr Ser Val Gly Asp Arg Val Ser
GAC GTC GTG ATG ACC CAG TCT CAA AAA TTC ATG TCC ACA TCA GTA GGA GAC AGG GTC AGC
Aat II
                                    30                                      40
Ile Thr Cys Lys Ala Ser Gln Asn Val Arg Thr Val Val Ala Trp Tyr Gln Gln Lys Pro
ATC ACC TGC AAG GCC AGT CAG AAT GTT CGT ACT GTT GTA GCC TGG TAT CAA CAG AAA CCA
                                    50                                      60
Gly Gln Ser Pro Lys Thr Leu Ile Tyr Leu Ala Ser Asn Arg His Thr Gly Val Pro Asp
GGG CAG TCT CCT AAA ACA CTG ATT TAC TTG GCC TCC AAC CGG CAC ACT GGA GTC CCT GAT
                                    70                                      80
Arg Phe Thr Gly Ser Gly Ser Gly Thr Asp Phe Thr Leu Thr Ile Ser Asn Val Gln Ser
CGC TTC ACA GGC AGT GGA TCT GGG ACA GAT TTC ACT CTC ACC ATT AGC AAT GTG CAA TCT
                                    90                                     100
Glu Asp Leu Ala Asp Tyr Phe Cys Leu Gln His Trp Ser Tyr Pro Leu Thr Phe Gly Ser
GAA GAC CTG GCA GAT TAT TTC TGT CTG CAA CAT TGG AGT TAT CCT CTC ACG TTC GGA TCC
                                                                        Bam HI

218 Linker                                 120
Gly Thr Lys Leu Glu Val Lys Gly Ser Thr Ser Gly Ser Gly Lys Pro Gly Ser Gly Glu
GGG ACA AAG TTG GAA GTA AAA GGT TCT ACC TCT GGT TCT GGT AAA CCC GGG AGT GGT GAA
                                                                  Sma I
```

A33 V$_H$

```
                                   130                                     140
Gly Ser Thr Lys Gly Glu Val Lys Leu Val Glu Ser Gly Gly Gly Leu Val Lys Pro Gly
GGT AGC ACT AAA GGT GAA GTG AAG CTT GTG GAG TCT GGG GGA GGC TTA GTG AAG CCT GGA
                               Hind III
                                   150                                     160
Gly Ser Leu Lys Leu Ser Cys Ala Ala Ser Gly Phe Ala Phe Ser Thr Tyr Asp Met Ser
GGG TCC CTG AAA CTC TCC TGT GCA GCC TCT GGA TTC GCT TTC AGT ACC TAT GAC ATG TCT
                                   170                                     180
Trp Val Arg Gln Thr Pro Glu Lys Arg Leu Glu Trp Val Ala Thr Ile Ser Ser Gly Gly
TGG GTT CGC CAG ACT CCG GAG AAG AGG CTG GAG TGG GTC GCA ACC ATT AGT AGT GGT GGT
                                   190                                     200
Ser Tyr Thr Tyr Tyr Leu Asp Ser Val Lys Gly Arg Phe Thr Ile Ser Arg Asp Ser Ala
AGT TAC ACC TAC TAT TTA GAC AGT GTG AAG GGC CGA TTC ACC ATC TCC AGA GAC AGT GCC
                                   210                                     220
Arg Asn Thr Leu Tyr Leu Gln Met Ser Ser Leu Arg Ser Glu Asp Thr Ala Leu Tyr Tyr
AGG AAC ACC CTA TAC CTG CAA ATG AGC AGT CTG AGG TCT GAG GAC ACG GCC TTG TAT TAC
                                   230                                     240
Cys Ala Pro Thr Thr Val Val Pro Phe Ala Tyr Trp Gly Gln Gly Thr Leu Val Thr Val
TGT GCA CCG ACT ACG GTA GTC CCG TTT GCT TAC TGG GGC CAA GGG ACT CTG GTC ACT GTC
                                   250
Ser
TCT TAA TAG ATCT
         Bgl II
```

FIG.13

LINKER FOR LINKED FUSION POLYPEPTIDES

CROSS-REFERENCE TO RELATED APPLICATIONS

This application is a continuation-in-part of U.S. patent application Ser. No. 08/002,845, filed Jan. 15, 1993, now abandoned which is a continuation-in-part of U.S. patent application Ser. No. 07/980,529, filed Nov. 20, 1992 now abandoned. All of these applications are incorporated herein by reference.

BACKGROUND OF THE INVENTION

1. Field of the Invention

The present invention relates to linked fusion polypeptides derived from single and multiple chain proteins. In particular, the invention relates to the linker peptide essential for bridging the polypeptide constituents that comprise the linked fusion polypeptide.

2. Description of the Background Art

The advent of modern molecular biology and immunology has brought about the possibility of producing large quantities of biologically active materials in highly reproducible form and with low cost. Briefly, the gene sequence coding for a desired natural protein is isolated, replicated (cloned) and introduced into a foreign host such as a bacterium, a yeast (or other fungi) or a mammalian cell line in culture, with appropriate regulatory control signals. When the signals are activated, the gene is transcribed and translated, and expresses the desired protein. In this manner, such useful biologically active materials as hormones, enzymes and antibodies have been cloned and expressed in foreign hosts.

One of the problems with this approach is that it is limited by the "one gene, one polypeptide chain" principle of molecular biology. In other words, a genetic sequence codes for a single polypeptide chain. Many biologically active polypeptides, however, are aggregates of two or more chains. For example, antibodies are three-dimensional aggregates of two heavy and two light chains. In the same manner, large enzymes such as aspartate transcarbamylase, for example, are aggregates of six catalytic and six regulatory chains, these chains being different. In order to produce such complex materials by recombinant DNA technology in foreign hosts, it becomes necessary to clone and express a gene coding for each one of the different kinds of polypeptide chains. These genes can be expressed in separate hosts. The resulting polypeptide chains from each host would then have to be reaggregated and allowed to refold together in solution. Alternatively, the two or more genes coding for the two or more polypeptide chains of the aggregate could be expressed in the same host simultaneously, so that refolding and reassociation into the native structure with biological activity will occur after expression. This approach, however, necessitates expression of multiple genes in a single host.

A classical example of multigene expression to form multimeric polypeptides is the expression by recombinant DNA technology of antibodies. Antibodies are iminunoglobulins typically composed of four polypeptides; two heavy chains and two light chains. Genes for heavy and light chains have been introduced into appropriate hosts and expressed, followed by reaggregation of these individual chains into functional antibody molecules (see, for example, Munro, *Nature* 312:597 (1984); Morrison, S. L., *Science* 229:1202' (1985); and Oi et al., *BioTechniques* 4:214 (1986); Wood et al., *Nature* 314:446–449 (1985)).

Antibody molecules have two generally recognized regions in each of the heavy and light chains. These regions are the so-called "variable" region which is responsible for binding to the specific antigen in question, and the so-called "constant" region which is responsible for biological effector responses such as complement binding, etc. The constant regions are not necessary for antigen binding. The constant regions have been separated from the antibody molecule, and biologically active (i.e., binding) variable regions have been obtained.

The variable regions of a light chain ($V_L$) and a heavy chain ($V_H$) together form the structure responsible for an antibody's binding capability. Light and heavy chain variable regions have been cloned and expressed in foreign hosts, and maintain their binding ability (Moore et al., European Patent Publication 0088994 (published Sep. 21, 1983) see also Cabilly, U.S. Pat. No. 4,816,567 (issued Mar. 28, 1989)). Antibodies may be cleaved to form fragments, some of which retain their binding ability. One such fragment is the "Fv" fragment, which is composed of the terminal binding portions of the antibodies. The Fv comprises two complementary subunits, the $V_L$ and $V_H$, which in the native antibody compose the binding domains.

The Fv fragment of an antibody is probably the minimal structural component which retains the binding characteristics of the parent antibody. The limited stability at low protein concentrations of the Fv fragments may be overcome by using an artificial peptide linker to join the variable domains of an Fv. The resulting single-chain Fv (hereinafter "sFv") polypeptides have been shown to have binding affinities equivalent to the monoclonal antibodies (MAbs) from which they were derived (Bird et at., *Science* 242:423 (1988)). In addition, catalytic MAbs may be converted to a sFv form with retention of catalytic characteristics (Gibbs et al., *Proc. Natl. Acad. Sci., USA* 88:4001 (1991)).

There are a number of differences between single-chain Fv (sFv) polypeptides and whole antibodies or antibody fragments, such as Fab or F(ab)'$_2$. Single-chain Fv polypeptides are small proteins with a molecular weight around 27 kd, which lack the constant regions of 50 kd Fab fragments or 150 kd immunoglobulin antibodies bearing gamma chains (IgG). Like a Fab fragment, and unlike an IgG, an sFv polypeptide contains a single binding site.

The in vivo properties of sFv polypeptides are different from MAbs and antibody fragments. Due to their small size, sFv polypeptides clear more rapidly from the blood and penetrate more rapidly into tissues (Colcher, et al., *J. Natl. Cancer Inst.* 82:1191 (1990); Yokota et al., *Cancer Research* 52:3402 (1992)). Due to lack of constant regions, sFv polypeptides are not retained in tissues such as the liver and kidneys. Due to the rapid clearance and lack of constant regions, sFv polypeptides will have low immunogenicity. Thus, sFv polypeptides have applications in cancer diagnosis and therapy, where rapid tissue penetration and clearance are advantageous.

Monoclonal antibodies have long been envisioned as magic bullets, in which they deliver to a specific tumor cell a cytotoxic agent in a highly targeted manner. sFv polypeptides can be engineered with the two variable regions derived from a MAb. The sFv is formed by ligating the component variable domain genes with an oligonucleotide that encodes an appropriately designed linker polypeptide. Typically, the linker bridges the C-terminus of the first V region and the N-terminus of the second V region. sFv polypeptides offer a clear advantage over MAbs because they do not have the constant regions derived from their biological source, which may cause antigenic reaction against the MAb. Single-chain immunotoxins have been produced by fusing a cell binding sFv with Pseudomonas exotoxin (Chaudhary et al., *Nature* 339:394 (1989)). Recently, a single-chain immunotoxin was shown to cause tumor regression in mice (Brinkmann et al., *Proc. Natl. Acad. Sci. USA* 88:8616 (1991)).

The general considerations behind the design and construction of polypeptide linkers as applied to sFv polypeptides have been previously described in U.S. Pat. No. 4,946,778 (Ladner et al.). Computer design of linkers has also been described in U.S. Pat. Nos. 4,704,692, 4,853,871, 4,908,773 and 4,936,666.

Four linkers are described in the '778 disclosure: TRY40, TRY59, TRY61, and TRY104b. TRY40 is a double linker with 3- and 7-amino acid sequences comprising the linkers. The sequences are PGS and IAKAFKN (see page 8, Table 1 for a description of the single letter amino acid code used herein). TRY59 is an 18-residue single linker having the sequence KESGSVSSEQLAQFRSLD (SEQ. ID No. 2). TRY61 is a 14-residue single linker having the sequence VRGSPAINVAVHVF (SEQ. ID No. 3). TRY104b is a 22-residue single linker constructed primarily of a helical segment from human hemoglobin. The sequence is AQGTLSPADKTNV KAAWGKVMT (SEQ. ID No. 4).

Traunecker et al., *EMBO J.* 10(12):3655–3659 (1991) have disclosed an 18-amino acid linker for joining the first two N-terminal CD4 domains and the combining site of the human CD3 complex. Its sequence is VEGGSGGS GGSGGSGGVD (SEQ. ID No. 5). The final bispecific single-chain polypeptide is called Janusin, and targets cytotoxic lymphocytes on HIV-infected cells.

Fuchs et al., *Bio/Technology* 9:1369–1372 (1991), used an 18-residue linker to join the heavy- and light-chain variable domains of a humanized antibody against chick lysozyme. The 18-residue linker was partially derived from α-tubulin and contains a MAb epitope specific to α-tubulin. The full sequence is GSASAPKLEEGEFSEARE (SEQ. ID No. 6).

A host of single-chain Fv analog polypeptides are disclosed in the literature (see, Huston, J. S. et al., *Proc. Natl. Acad. Sci. USA* 85:5879–5883 (1988); Huston, J. S. et al., *SIM News* 38(4) (Suppl.):11 (1988); McCartney, J. et al., *ICSU Short Reports* 10:114 (1990); McCartney, J. E. et al., unpublished results (1990); Nedelman, M. A. et al., *J. Nuclear Med.* 32 (Suppl.):1005 (1991); Huston, J. S. et al., In: *Molecular Design and Modeling: Concepts and Applications*, Part B, edited by J. J. Langone, *Methods in Enzymology* 203:46–88 (1991); Huston, J. S. et al., In: *Advances in the Applications of Monoclonal Antibodies in Clinical Oncology*, Epenetos, A. A. (Ed.), London, Chapman & Hall (1993); Bird, R. E. et al., *Science* 242:423–426 (1988); Bedzyk, W. D. et al., *J. Biol. Chem.* 265:18615–18620 (1990); Colcher, D. et al., *J. Nat. Cancer Inst.* 82:1191–1197 (1990); Gibbs, R. A. et al., *Proc. Natl. Acad. Sci. USA* 88:4001–4004 (1991); Milenic, D. E. et al., *Cancer Research* 51:6363–6371 (1991); Pantoliano, M. W. et al., *Biochemistry* 30:10117–10125 (1991); Chaudhary, V. K. et al., *Nature* 339:394–397 (1989); Chaudhary, V. K. et al., *Proc. Natl. Acad. Sci. USA* 87:1066–1070 (1990); Batra, J. K. et al., *Biochem. Biophys. Res. Comm.* 171:1–6 (1990); Batra, J. K. et al., *J. Biol. Chem.* 265:15198–15202 (1990); Chaudhary, V. K. et al., *Proc. Natl. Acad. Sci. USA* 87:9491–9494 (1990); Batra, J. K. et al., *Mol. Cell. Biol.* 11:2200–2205 (1991); Brinkmann, U. et al., *Proc. Natl. Acad. Sci. USA* 88:8616–8620 (1991); Seetharam, S. et al., *J. Biol. Chem.* 266:17376–17381 (1991); Brinkmann, U. et al., *Proc. Natl. Acad. Sci. USA* 89:3075–3079 (1992); Glockshuber, R. et al., *Biochemistry* 29:1362–1367 (1990); Skerra, A. et al., *Bio/Technol.* 9:273–278 (1991); Pack, P. et al., *Biochem.* 31:1579–1534 (1992); Clackson, T. et al., *Nature* 352:624–628 (1991); Clackson, T. et al., *Nature* 352:624–628 (1991); Marks, J. D. et al., *J. Mol. Biol.* 222:581–597 (1991); Iverson, B. L. et al., *Science* 249:659–662 (1990); Roberts, V. A. et al., *Proc. Natl. Acad. Sci. USA* 87:6654–6658 (1990); Condra, J. H. et al., *J. Biol. Chem.* 265:2292–2295 (1990); Laroche, Y. et al., *J. Biol. Chem.* 266:16343–16349 (1991); Holvoet, P. et al., *J. Biol. Chem.* 266:19717–19724 (1991); Anand, N. N. et al., *J. Biol. Chem.* 266:21874–21879(1991); Fuchs, P. et al., *Bio/Technol.* 9:1369–1372 (1991); Breitling, F. et al., *Gene* 104:104–153 (1991); Seehaus, T. et al., *Gene* 114: in press (1992); Takkinen, K. et al., *Prot. Eng.* 4:837–841 (1991); Dreher, M. L. et al., *J. Immunol. Methods* 139:197–205 (1991); Mottez, E. et al., *Eur. J. Imunol.* 21:467–471 (1991); Traunecker, A. et al., *Proc. Natl. Acad. Sci. USA* 88:8646–8650 (1991); Traunecker, A. et al., *EMBO J.* 10:3655–3659 (1991); Hoo, W. F. S. et al., *Proc. Natl. Acad. Sci. USA* 89:4759–4763 (1993)). Linker lengths used in those Fv analog polypeptides vary from 10 to 28 residues.

Linkers previously used for sFvs and other polypeptides suffer from proteolytic attack, rendering them less stable and prone to dissociation. They also suffer from inordinate aggregation at high concentrations, making them susceptible to concentration in the liver and kidneys. Therefore, there is a need for more stable linkers that are resistant to proteolytic attack and less prone to aggregation.

SUMMARY OF THE INVENTION

The invention is directed to a linked fusion polypeptide comprising polypeptide constituents connected by a novel peptide linker. The novel peptide linker comprises a sequence of amino acids numbering from about 2 to about 50 having a first end connected to a first protein domain, and having a second end connected to a second protein domain, wherein the peptide comprises at least one proline residue within the sequence, the proline being positioned next to a charged amino acid, and the charged amino acid-proline pair is positioned within the peptide linker to inhibit proteolysis of said polypeptide.

The invention is also directed to a novel peptide linker comprising the amino acid sequence:

$U_m XPZ_n$ (SEQ. ID NO 24)

wherein the numbering order from left to right (amino to carboxyl) is up to 50 residues, U and Z can be single natural amino acids, homopolymers of natural amino acids, or heteropolymers of natural amino acids, such that n and m are any integers from 0 to 48 and n+m is not greater than 48, and X is a charged amino acid. In a preferred embodiment, however, X is lysine or arginine and at least one of the $U_m$ and $Z_n$ sequences comprises at least one alternating glycine-serine sequence.

The more preferable peptide linker comprises the amino acid sequence:

GSTSGSGXPGSGEGSTKG (SEQ. ID NO 1), wherein the numbering order from left to right (amino to carboxyl) is 1 to 18, and X is a charged amino acid. In a preferred embodiment X is lysine or arginine.

The invention also relates to sFv's wherein the linker linking $V_H$ and $V_L$ regions is the peptide linker as herein described, preferably comprising from about 10 to about 30 amino acids, and more preferably comprising at least 18 amino acids.

The invention also relates to non-covalently bound multivalent Fvs wherein the linker linking two variable regions is the peptide linker comprising the amino acid sequence:

GSTSGXPSEGKG (SEQ. ID NO. 25)

wherein the numbering order from left to right (amino to carboxyl) is 1 to 12, and X is a charged amino acid. In a preferred embodiment X is lysine or arginine. Two or more of the linked polypeptides associate non-covalently to form a multivalent Fv.

The invention also relates to genetic sequences encoding linked fusion polypeptides containing the novel peptide linker herein described, methods of making such linked fusion polypeptides, and methods of producing such linked fusion polypeptides via recombinant DNA technology.

BRIEF DESCRIPTION OF THE DRAWINGS

FIG. 3 is the amino acid (SEQ. ID No. 12) and nucleotide (SEQ. ID No. 11) sequence of the linked fusion polypeptide comprising the 4-4-20 $V_L$ region connected through the 217 linker to the CC49 $V_H$ region.

FIG. 4 is the amino acid (SEQ. ID No. 14) and nucleotide (SEQ. ID No. 13) sequence of the linked fusion polypeptide comprising the CC49 $V_L$ region connected through the 217 linker polypeptide to the 4-4-20 $V_H$ region.

FIG. 12 is the amino acid sequence (SEQ ID No. 16) and nucleotide sequence (SEQ ID No. 15) of the A33/212 sFv.

FIG. 13 is the amino acid sequence (SEQ ID No. 18) and nucleotide sequence (SEQ ID No. 17) of the A33/218 sFv.

DEFINITIONS

Amino acid Codes

Figure 1A:
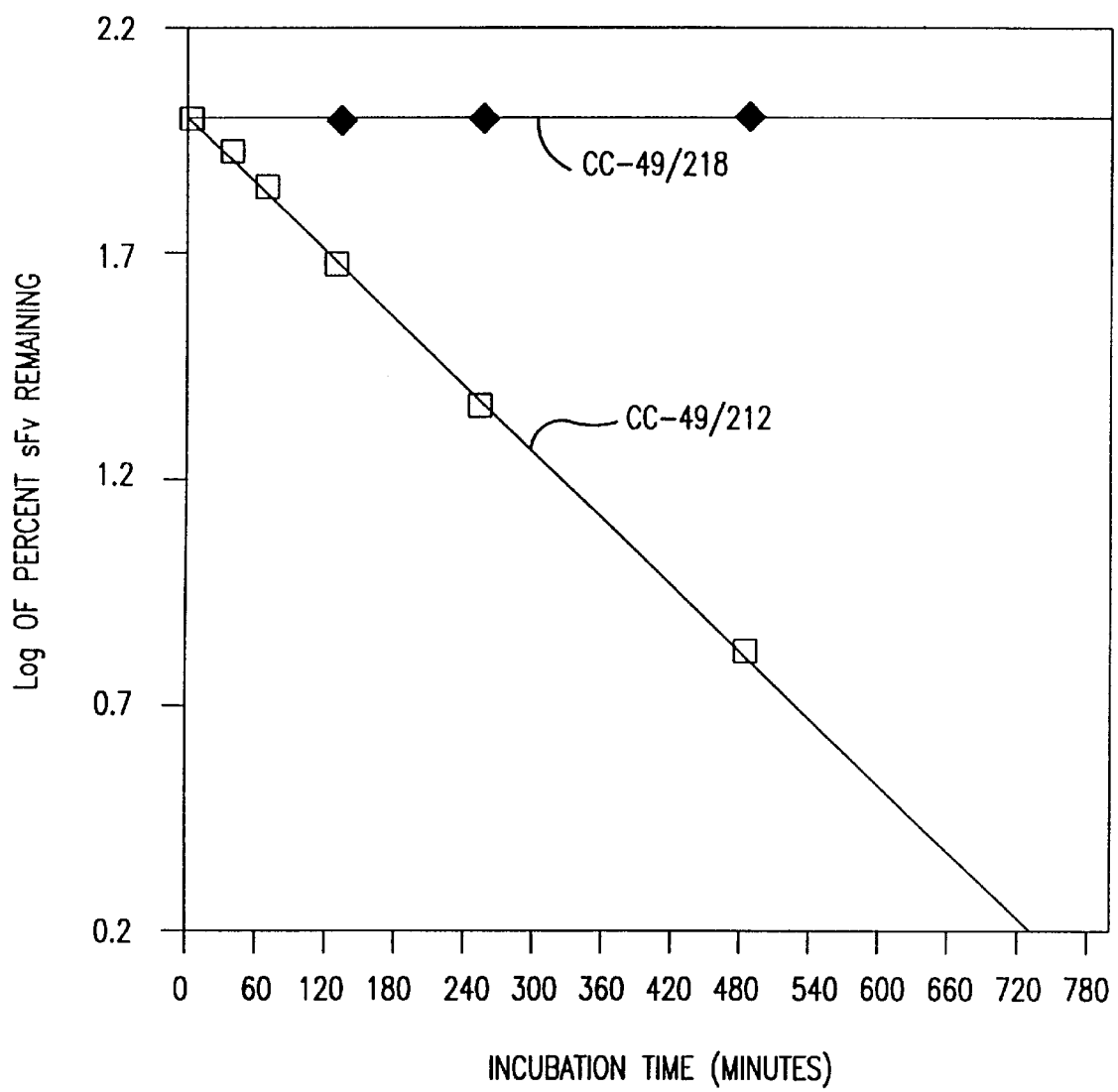
FIG. 1A–1B is a set of two graphs depicting the proteolytic susceptibility of the CC49/212 and CC49/218 sFv proteins when exposed to subtilisin BPN' (FIG. 1A) or trypsin (FIG. 1B). The fraction of sFv remaining intact was determined by reverse phase HPLC. The CC49/212 sFv is shown in open circles and the CC49/218 is shown in closed squares. There was no measurable degradation of the CC49/218 sFv.

The most common amino acids and their codes are described in Table 1:

TABLE 1

| Amino acid names and codes | |
|---|---|
| Amino acid | Single letter code |
| Alanine | A |
| Arginine | R |
| Aspartic acid | D |
| Asparagine | N |
| Cysteine | C |
| Glutamic acid | E |
| Glutamine | Q |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

Protein

As referred to herein, a protein is a biological molecule which consists primarily of one or more polypeptides. A protein consisting of a single polypeptide is referred to herein as a single chain protein. A protein consisting of more than one polypeptide is referred to herein as a multi-chain protein, with the term chain being synonymous with the term polypeptide.

Polypeptide

As referred to herein, a polypeptide is a linear, single chain polymer of multiple amino acids linked through their amino and carboxylate groups by peptide bonds. A polypeptide may form a single chain protein by itself or, in association with other polypeptides, form a multi-chain protein. A polypeptide may also be a fragment of a single chain protein or a fragment of one of the chains of a multi-chain protein.

Linked fusion polypeptide

As referred to herein, a linked fusion polypeptide is a polypeptide made up of two smaller polypeptide constituents, each constituent being derived from a single chain protein or a single chain of a multi-chain protein, where the constituents are combined in a non-naturally occurring arrangement using a peptide linker. Linked fusion polypeptides mimic some or all of the functional aspects or biological activities of the protein(s) from which their polypeptide constituents are derived. The constituent at the amino terminal portion of the linked fusion polypeptide is referred to herein as the first polypeptide. The constituent at the carboxy terminal portion of the linked fusion polypeptide is referred to herein as the second polypeptide. By "non-naturally occurring arrangement" is meant an arrangement which occurs only through in vitro manipulation of either the polypeptide constituents themselves or the nucleic acids which encode them.

Peptide linker

As referred to herein, a peptide linker or linker is a polypeptide typically ranging from about 2 to about 50 amino acids in length, which is designed to facilitate the functional connection of two polypeptides into a linked fusion polypeptide. The term functional connection denotes a connection that facilitates proper folding of the polypeptides into a three dimensional structure that allows the linked fusion polypeptide to mimic some or all of the functional aspects or biological activities of the protein(s) from which its polypeptide constituents are derived. In cases such as sFv polypeptides where the linker is used to make a single chain derivative of a multi-chain protein, to achieve the desired biological activity the appropriate three dimensional structure will be one that mimics the structural relationship of the two polypeptide constituents in the native multi-chain protein. The term functional connection also denotes a connection that confers a degree of stability required for the resulting linked fusion polypeptide to function as desired.

Charged Amino Acid

As referred to herein, a charged amino acid is a biologically derived amino acid which contains a charge at neutral pH. Charged amino acids include the negatively charged amino acids Aspartic acid (D) and Glutamic acid (E) as well as positively charged amino acids Histidine (H), Lysine (K), and Arginine (R).

Immunoglobulin superfamily

As referred to herein, the immunoglobulin superfamily is the family of proteins containing one or more regions that resemble the variable or constant regions of an immunoglobulin, or fundamental structural units (i.e., domains) found within these regions. The resemblance referred to is in terms of size, amino acid sequence, and presumably three dimensional structure. Members of the immunoglobulin superfamily typically mediate non-enzymatic intercellular surface recognition and include, but are not limited to, CD1, CD2, CD3, CD7, CD8, CD28 class I and II histocompatibility molecules, Beta-2 microglobulin, lymphocyte function associated antigen-3 (LFA-3), $Fc_\gamma$ receptor, Thy-1, T cell receptor, polyimmunoglobulin receptor, neuronal cell adhesion molecule, myelin associated glycoprotein, $P_o$ myelin, carcinoembryonic antigen, platelet derived growth factor receptor, colony stimulating factor-1 receptor, link protein of basement membrane, and $\alpha_1\beta$-glycoprotein.

T cell Receptor

As referred to herein, T cell receptor is a member of the immunoglobulin superfamily that resides on the surface of T lymphocytes and specifically recognizes molecules of the major histocompatibility complex, either alone or in association with foreign antigens.

Immunoglobulin

As referred to herein, an iminunoglobulin is a multi-chain protein with antibody activity typically composed of two types of polypeptides, referred to as heavy and light chains. The heavy chain is larger than the light chain and typically consists of a single variable region, three or four constant regions, a carboxy-terminal segment and, in some cases, a hinge region. The light chain typically consists of a single variable region and a single constant region.

Antibody

As referred to herein, an antibody is an iminmunoglobulin that is produced in response to stimulation by an antigen and that reacts specifically with that antigen. Antibodies are typically composed of two identical heavy and two identical light polypeptide chains, held together by interchain disulfide bonds.

Single chain Fv polypeptide (sFv)

As referred to herein, a single chain Fv polypeptide (sFv) is a linked fusion polypeptide composed of two variable regions derived from the same antibody, connected by a peptide linker. An sFv is capable of binding antigen similar to the antibody from which its variable regions are derived. An sFv composed of variable regions from two different antibodies is referred to herein as a mixed sFv. A multivalent sFv is composed of two or more non-covalently linked single-chain sFv's.

DETAILED DESCRIPTION OF THE INVENTION

In order to design a peptide linker that will join any multichain protein to form a linked fusion polypeptide with the same or similar function as the multi-chain protein, it is necessary to define the extent of each chain that must be included. For example, to design a peptide linker that will join the variable domains of an antibody to form an sFv, the extent of the variable domains must first be defined. Kabat et al. (Kabat et al., Sequences of Proteins of Immunological Interest, Department of Health and Human Services, Fourth Edition, U.S. (1987)) defines the variable domain ($V_L$) to extend from residue 1 to residue 107 for the lambda light chain, and to residue 108 for kappa light chains, and the variable domain of the heavy chain ($V_H$) to extend from residue 1 to residue 113.

Single-chain Fvs can and have been constructed in several ways. Either $V_L$ is the N-terminal domain followed by the linker and $V_H$ (a $V_L$-Linker-$V_H$ construction) or $V_H$ is the N-terminal domain followed by the linker and $V_L$ ($V_H$-Linker-$V_L$ construction). Alternatively, multiple linkers have also been used. Several types of sFv proteins have been successfully constructed and purified, and have shown binding affinities and specificities similar to the antibodies from which they were derived.

Typically, the Fv domains have been selected from the group of monoclonal antibodies known by their abbreviations in the literature as 26–10, MOPC 315, 741F8, 520C9, McPC 603, D1.3, murine phOx, human phOx, RFL3.8 sTCR, 1A6, Se155-4, 18-2-3, 4-4-20, 7A4-1, B6.2, CC49, 3C2, 2c, MA-15C5/$K_{12}G_0$, Ox, etc. (see references previously cited as disclosing Fv analog polypeptides). One of ordinary skill in the art will be able to adapt a linker to join other domains not mentioned herein. The Fv's are derived from the variable regions of the corresponding monoclonal antibodies (MAbs).

Linkers have also been used to join non-antibody polypeptides, as evidenced by Soo Hoo et al., *Proc. Natl. Acad. Sci. USA* 89:4759–4763 (1992) and Kim et al. *Protein Engineering* 2(8):571–575 (1989). Soo Hoo et al. discloses a linker connecting the variable regions of the α and β chains of a T cell receptor. Kim et al. discloses a linker designed to link the two polypeptide chains of monellin, a multi-chain protein known for its sweet taste.

Thus, it is envisioned that linkers according to the invention will be useful for connecting polypeptides derived from any protein. The order in which the polypeptides are connected (i.e., which is nearer the amino or carboxy terminus of the linked fusion polypeptide) should, where possible, reflect the relationship of the polypeptides in their native state. For example, consider a linked fusion polypeptide derived from two chains of a multi-chain protein where the amino terminal portion of the first chain is normally associated (i.e., in proximity to) the carboxy terminal portion of the second chain. In this case, the polypeptide derived from the first chain should be positioned near the amino-terminal portion of the linked fusion polypeptide and the polypeptide derived from the second chain should be positioned near the carboxy-terminal portion.

In particular, it is envisioned that linkers according to the invention will be applicable to any multi-chain protein or protein complex including, but not limited to, members of tile immunoglobulin superfamily, enzymes, enzyme complexes, ligands, regulatory proteins, DNA-binding proteins, receptors, hormones, etc. Specific examples of such proteins or protein complexes include, but are not limited to, T cell receptors, insulin, RNA polymerase, Myc, Jun, Fos, glucocorticoid receptor, thyroid hormone receptor, acetylcholine receptor, fatty acid synthetase complex, hemoglobin, tubulin, myosin, β-Lactoglobulin, aspartate transcarbamoylase, malic dehydrogenase, glutamine synthetase, hexokinase, glyceraldehyde-phosphate dehydrogenase, glycogen phosphorylase, tryptophan synthetase, etc.

It is also envisioned that non-polypeptide biochemical moieties including, but not limited to, toxins, drugs, radioisotopes, etc. may be added to, or associated with, the linked fusion polypeptides to achieve a desired effect, such as labeling or conferring toxicity.

The preferred length of the peptide linker should be from 2 to about 50 amino acids. In each particular case, the preferred length will depend upon the nature of the polypeptides to be linked and the desired activity of the linked fusion polypeptide resulting from the linkage. Generally, the linker should be long enough to allow the resulting linked fusion polypeptide to properly fold into a conformation providing the desired biological activity. Where conformational information is available, as is the case with sFv polypeptides discussed below, the appropriate linker length may be estimated by consideration of the 3-dimensional conformation of the substituent polypeptides and the desired conformation of the resulting linked fusion polypeptide. Where such information is not available, the appropriate linker length may be empirically determined by testing a series of linked fusion polypeptides with linkers of varying lengths for the desired biological activity.

Linkers of the invention used to construct sFv polypeptides are designed to span the C terminus of $V_L$ (or neighboring site thereof) and the N terminus of $V_H$ (or neighboring site thereof) or between the C terminus of $V_H$ and the N terminus of $V_L$. The linkers used to construct sFv polypeptides have between 10 and 30 amino acid residues. The linkers are designed to be flexible, and it is recommended that an underlying sequence of alternating Gly and Ser residues be used.

To enhance the solubility of the linker and its associated single chain Fv protein, three charged residues may be included, two positively charged lysine residues (K) and one negatively charged glutamic acid residue (E). Preferably, one of the lysine residues is placed close to the N-terminus of $V_H$, to replace the positive charge lost when forming the peptide bond of the linker and the $V_H$.

In addition, it has unexpectedly been found that linker lengths of equal to or greater than 18 residues reduce aggregation. This becomes important at high concentrations, when aggregation tends to become evident. Thus, linkers having 18 to 30 residues are preferred for sFv polypeptides.

Another property that is important in engineering an sFv polypeptide, or any other linked fusion polypeptide, is proteolytic stability. The 212 linker (Pantoliano et al., *Biochemistry* 30:10117 (1991)) is susceptible to proteolysis by subtilisin BPN'. The proteolytic clip in the 212 linker occurs between Lys8 and Ser9 of the linker (see Table 2). By placing a proline at the proteolytic clip site one may be able to protect the linker. The inventors, not wishing to be bound by any particular theory of operation, postulate that the proline residue in the peptide linker of the present invention inhibits the charge-transfer intermediate that is essential to the hydrolysis of the amide bond joining the two amino acid residues clipped apart by serine proteases.

Table 2 shows two of the claimed linkers (217 and 218) and two of the prior art linkers (202' and 212) for illustration. The 217 linker contains a lysine-proline pair at positions 6 and 7; the 218 linker contains the lysine-proline pair at positions 8 and 9, respectively, thus rendering the linker less susceptible to proteolysis. The 218 linker demonstrates less aggregation, greater proteolytic stability, and the necessary flexibility and solubility to result in a functional linker for sFv proteins. Holliger et al., PNAS, USA 90:6444–6448 (1993) have demonstrated that linkers of 0 to 5 residues in length facilitate the formation of divalent Fvs. The 217 linker was designed for divalent Fvs, where the association (aggregation) of two sFv polypeptides is required.

TABLE 2

Linker Designs $V_L$-Linker-$V_H$ Construction

| $V_L$ | Linker | $V_H$ | Linker Name | Reference |
|---|---|---|---|---|
| -KLEIE | GKSSGSGSESKS[3] | TQKLD- | 202' | Bird et al.[1] |
| -KLEIK | GSTSGSGKSSEGKG[4] | EVKLD- | 212 | Bedzyk et al.[2] |
| -KLEIK | GSTSGSGKSSEGSGSTKG[5] | EVKLD- | 216 | 212 Experimental Derivative |
| -KLVLK | GSTSGKPSEGKG[6] | EVKLD- | 217 | Invention |
| -KLEIK | GSTSGSGKPGSGEGSTKG[7] | EVKLD- | 218 | Invention |

[1]Science 242:423 (1988)
[2]JBC 265:18615-18620 (1990)
[3]SEQ. ID No. 7
[4]SEO. ID No. 8
[5]SEQ. ID No. 9
[6]Part of SEQ. ID No. 12
[7]SEQ. ID No. 10

The stability and affinity of an antifluorescein single-chain Fv's has been previously reported (Pantoliano, M. W., et al., Biochemistry 30:10117–10125 (1991)). The data in the prior studies showed that the affinity of the 4-4-20 sFvs for fluorescein may increase with longer linkers. The data was not conclusive for the longest linker, 205, which was thought to be helical. Thus, a 4-4-20 sFv was designed, constructed, purified and assayed with an 18 residue linker that was four residues longer than the 212 linker (see Table 2). This new linker was designated 216. The anti-fluorescein sFvs 4-4-20/202', 4-4-20/212 and 4-4-20/216 had affinities of $0.5 \times 10^9$ $M^{-1}$, $1.0\times10^9$ $M^{-1}$, and $1.3\times10^9$ $M^{-1}$, respectively using the fluorescence quenching assay.

In attempting to crystalize the anti-fluorescein 4-4-20 sFvs, they were concentrated to over 10 mg/ml. At these high concentrations it was noticed that they produced aggregates under a wide variety of conditions, as judged by size-exclusion HPLC chromatography. Although aggregation can be reversed by diluting the sample, it is an undesirable phenomenon. It was discovered that shorter linkers showed higher degrees of aggregation than larger linkers. For example, at 5 mg/ml the 4-4-20/202' sFv sample was 53% aggregated, whereas the 4-4-20/212 and 4-4-20/216 samples showed 34% and 10% aggregation, respectively.

A second discovery made in trying to crystallize the anti-fluorescein 4-4-20 sFvs was that the prior art 212 linker was proteolytically susceptible. It was possible to produce crystals of the 4-4-20/212 sFv only after it had been treated with subtilisin BPN', a serine protease. When 4-4-20/212 sFv and subtilisin BPN' were mixed in a 5000 to 1 ratio, the 27 kD band of the sFv was converted into two bands that ran just below the 14 kD marker on the SDS-PAGE. N-terminal sequencing of the clipped sFv showed that the prior art 212 linker had been clipped between the Lys 8 and Ser 9. The effective result of this clip was to change a sFv into an Fv, a much less stable molecule.

Without being bound to any particular theory underlying the invention, the inventors believe that the following discussion may explain the markedly improved characteristics of the 218 linker and other such linkers. In order to reduce the proteolytic susceptibility of the sFvs it is possible to protect the susceptible peptide bond between Lys 8 and Ser 9 in the linker of the invention. Most proteases are unable to cleave peptide-located bonds prior to a proline. This is because prolines do not have amide hydrogens. The proline side chain forms a five-membered ring with the amide nitrogen. It is believed that the five-membered ring of the proline prohibits proteolysis from occurring. It is believed that proline is unique in its ability to so inhibit proteolysis. Placement of the proline next to a charged residue is also preferred. The sequence of proline and a charged amino acid residue should be maintained with the charged residue before (i.e., on the amino-terminus side of) the proline. In a preferred embodiment, a lysine-proline pair is located at the cleavage site, replacing the susceptible amide bond that was hydrolyzed. In a second preferred embodiment, arginine may be used as the charged residue.

A second guiding consideration in designing the linker of the invention is that a linker with reduced aggregation is preferable. As described above, the 18-residue 216 linker shows reduced aggregation as compared to the 14-residue 212 linker. The first eleven residues of the 216 linker are identical to the 212 linker, including the proteolytically-susceptible peptide bond between Lys 8 and Ser 9. Thus, it is believed that the extra four residues contribute to the lowered aggregation. Linkers with 18 or more residues are thus preferred.

Taking the above into consideration, a new linker was designed in which a proline was substituted for serine at position 9, after Lys 8, in the 18-residue 216 linker. This linker was then subjected to testing in order to prove that it has the characteristics it was designed to have. The new linker was designated 218 (see Table 2).

Positioning the proline at the proper place in the linker sequence to inhibit proteolysis is accomplished by determining the points of proteolytic attack in the susceptible sequence. One of ordinary skill in the art will know of methods of determining this point. In one method, a protease such as subtilisin BPN' is contacted with the candidate linker. Cleavage can then be determined by sequencing the resulting peptides, which will also reveal the cleavage point or points, if any. Any protease may be used, and selection will be guided by consideration of the environment the linker is to encounter in actual use.

For each class of protein in which two or more polypeptides are linked by polypeptide linkers, the requirements of linker length will be different. The requirements for a sFv is that the linker be longer than 12 amino acids. The preferred length of the linker in a sFv is greater than 18 residues, in order to reduce aggregation, as described above.

For multivalent Fv's the association of two or more sFv's is required for their formation. Although, multivalent Fv's can be produced from sFv's with linkers as long as 25 residues, they tend to be unstable. Holliger et al., *PNAS, USA* 90:6444–6448 (1993) has recently demonstated that linkers 0 to 5 residues in length facilitate the formation of divalent Fvs. We designed the 12 residue 217 linker for bispecific CC49/4-4-20 $Fv_2$, where the association of two sFv polypeptides is required to form a divalent $Fv_2$.

Also provided by the invention are DNA molecules such as isolated genetic sequences or plasmids or vectors encoding linked fusion polypeptides with the peptide linker of the invention. The DNA sequence for the linked fusion polypeptide can be chosen so as to optimize production in organisms such as bacteria or yeast.

Recombinant hosts as well as methods of using them to produce single chain proteins by expression, are also provided herein.

The appropriate DNA molecules, hosts, methods of production, isolation and purification of linked fusion polypeptides, especially sFv polypeptides, are thoroughly described in the prior art, such as e.g., U.S. Pat. No. 4,946,778, which is fully incorporated herein by reference.

EXAMPLES

1. General Test Conditions

Cloning and Genetic Constructions. The cloning of the 4-4-20 variable domains has been previously described by Bedzyk, W. D., et al., *J. Biol. Chem.* 264:1565–1569 (1989). The sequence of the variable domain of the CC49 domain has been previously described by Mezes, P., et al., European Pat. Application No. EP 0 365 997 (1989). The genetic construction of the 4-4-20/202', 4-4-20/212 and CC49/212 sFvs have been previously described by Bedzyk, W. D., et al., *J. Biol. Chem.* 265:18615–18620 (1990) or Pantoliano, M. W., et al., *Biochemistry* 30:10117–10125 (1991) and Milenic, D., et al., *Cancer Res.* 51:6363–6371 (1991), respectively.

Purification. The purification of sFv polypeptides has been previously described by Pantoliano, M. W., et al., *Biochemistry* 30:10117–10125 (1991) and Whitlow and Filpula, *Methods* 2:97–105 (1991). Most of the sFv polypeptides were purified with a minor procedural modification, omitting the initial cation exchange HPLC step using the RCM Waters Accell Plus GM ion exchange (RCM) column.

Association constants of the anti-fluorescein sFvs. The association constants were determined for each of the anti-fluorescein sFvs following the procedures described by Herron and Voss, in *Fluorescence Hapten: An Immunological Probe*, E. W. Voss, Jr., ed., CRC Press, Boca Raton, Fla., 77–98 (1984).

Aggregation Rates. The rates of aggregation of the sFv polypeptides were determined at room temperature in 60 mM MOPS, pH 7.0 at various concentrations using Gel Filtration HPLC Chromatography. 10 to 50 μl samples were injected onto a Waters HPLC system with 7.8 mm×300 mm TSK G3000SW column (Toso Haas, Tokyo, Japan). The column had been previously equilibrated and the samples were eluted using 50 mM MOPS, 100 mM NaCl, buffer pH 7.5 at a flow rate of 0.5 ml/min. The data was collected on a MacIntosh SE (Apple Computer, Cupertino, Calif.) running the Dynamac software package (Rainin Instrument Co, Woburn, Mass.).

Radiolabeling of Proteins. MAb CC49 and CC49 sFv polypeptides were labeled with $Na^{125}I$ using Iodo-Gen (Pierce Chemical Co., Rockford, Ill.) as previously reported (Milenic, D., et al., *Cancer Res.* 51:6363–6371 (1991)).

The CC49 sFv polypeptides were labeled with the lutetium complex of the macrocyclic bifunctional coordinator PA-DOTA (Cheng et al., European Patent Application No. 353,450). 20 μl of a 1 mM solution of SCN-PA-DOTA in water was mixed with equal volumes of the $^{177}Lu(NO_3)_3$ solution and 1M HEPES buffer pH 7.0 and left at room temperature for five minutes. $^{177}Lu$ in 0.05N HCl was obtained from the University of Missouri Research Reactor (Columbia, Mo.). The reaction mixture was processed over a PRP-1 reverse-phase cartridge (Hamilton Co., Reno, Nev.) which had been equilibrated with 10% acetonitrile in 20 mM sodium carbonate, pH 9.5. $^{77}Lu$-SCN-PA-DOTA was eluted with acetonitrile/carbonate buffer (1:2) and a 60 μl fraction containing the radioactive chelate was used.

1 mg of each CC49 sFv was exchanged with 20 mM sodium carbonate, pH 9.5 buffer, then made to 980 μl with the same buffer. The sample was mixed with 20 ml of the $^{177}Lu$-SCN-PA-DOTA solution and left for 3 hours at 37° C., followed by PD-10 isolation as above. Both radiolabeling procedures resulted in >90% acid-precipitable counts.

2. Proteolytic Susceptibility of the 218 Linker $1.0 \pm 0.1 \times 10^{-5}M$ CC49/212 and CC49/218 sFv polypeptides were treated either with $2.6 \times 10^{-7}M$ subtilisin BPN' (Type XXVII protease, Sigma, St. Louis, Mo.) or with $7.7 \times 10^{-7}M$ trypsin at 37° C. The percent sFv remaining was monitored by reverse phase HPLC at various times. A non-linear gradient between 5% acetonitrile, 0.1% TFA and 70% acetonitrile, 0.1% TFA was run on a PLRP-S column (Polymer Labs., Church Stretton, England) in a heating unit (Timberline Instruments, Boulder, Colo.) on a waters HPLC system, following the procedures of Nugent, K. D., *Am. Biotechnol. Lab.*, pp. 24–32 (May 1990). The data was collected on a MacInosh SE (Apple Computer, Cupertino, Calif.) running the Dynamac software package (Rainin Instrument Co, Woburn, Mass.). The half-life ($t_{1/2}$) was determined from plots of the log of the fraction of sFv remaining versus time (FIGS. 1A–1B).

Figure 1B:
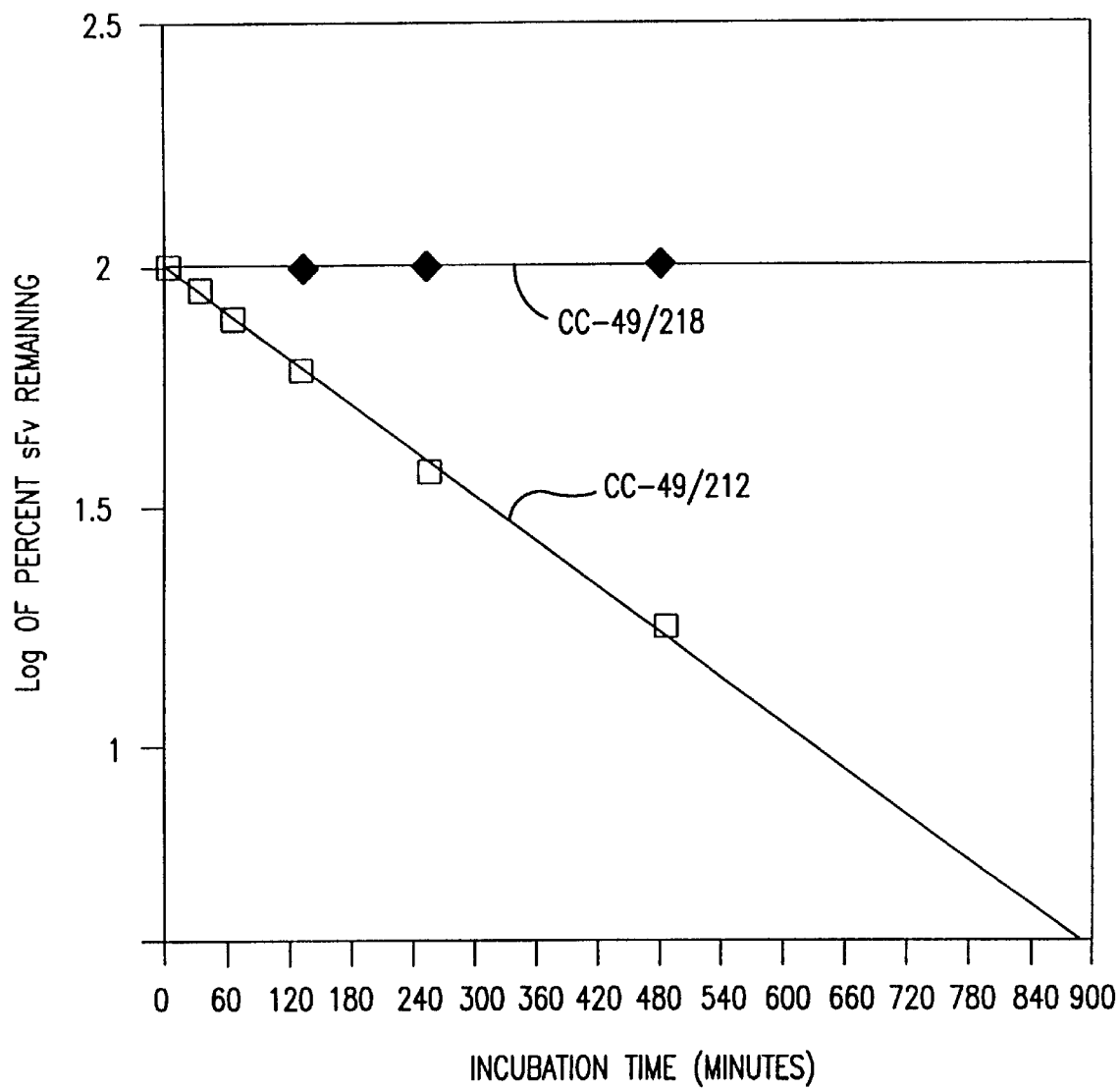

The half-life of the CC49/212 sFv treated with subtilisin or trypsin is 122.8 min and 195.7 min, respectively (see FIGS. 1A–1B). The 218 linker had significantly improved protease resistance, for in the 48 hour period digestion of the CC49/218 sFv was not detectable using either subtilisin or trypsin.

3. Binding Affinity with the 218 Linker

To determine the binding properties of the CC49 sFv polypeptides a competition radioimmunoassay (RIA) was set up in which a CC49 IgG labeled with 125I was competed against the unlabeled CC49 sFvs for binding to TAG-72 on a human breast carcinoma extract as previously described by Milenic, D., et al., *Cancer Res.* 51:6363–6371 (1991).

Figure 2:
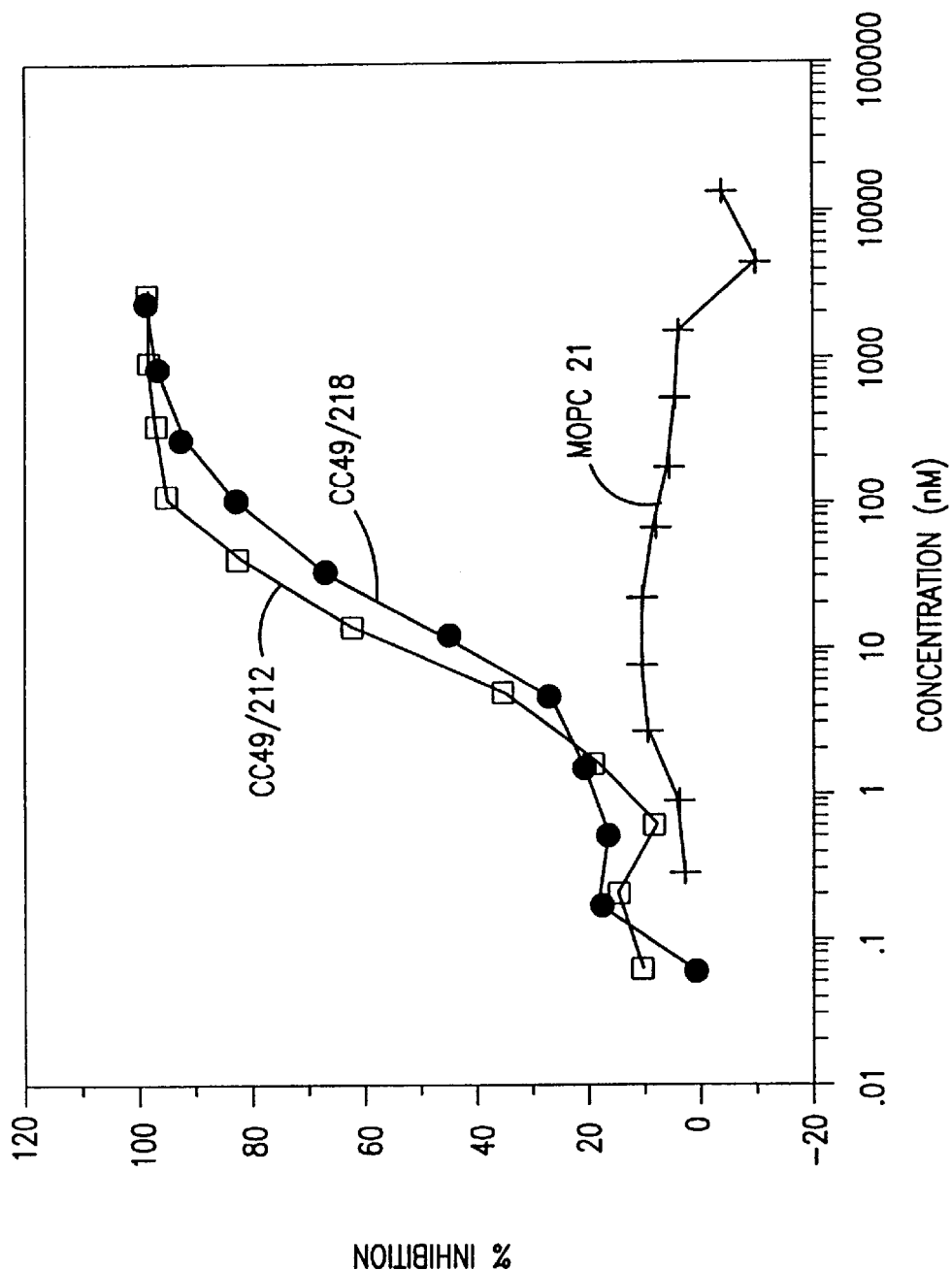
FIG. 2 is a graph depicting the results of a competition radioimmunoassay (RIA) in which unlabeled CC49/212 single-chain Fv (open squares), CC49/218 single-chain Fv (closed diamonds) or MOPC-21 IgG (+) competed against a CC49 IgG radiolabeled with $^{125}$I for binding to the TAG-72 antigen on a human breast carcinoma extract. MOPC-21 is a control antibody that does not bind to TAG-72 antigen.

The binding affinities for the TAG-72 antigen of the CC49/212 and CC49/218 sFv polypeptides were checked. The CC49/218 sFv (CC49/$V_H$ and CC49 $V_L$ connected by a 218 polypeptide linker) showed about a 4-fold lower affinity than the CC49/212 sFv (see FIG. 2). The lower affinity of the CC49/218 sFv could be in part due to the higher degree of aggregation of the CC49/212 sFv sample. We have shown previously that the dimeric forms of CC49 (IgG and F(ab')$_2$) compete with a ten-fold higher affinity than do the monovalent forms (Fab and sFv) (Milenic, D., et al., *Cancer Res.* 51:6363–6371 (1991)). Since aggregates are multivalent it seems likely that they would have high affinity.

4. Aggregation Rates with 218 Linker

The rates of aggregation of the CC49/212 and CC49/218 sFv polypeptides were determined at room temperature (22° C.) at various concentrations. The CC49/212 sFv showed 80-fold faster accumulation of aggregates than did the CC49/218 sFv, at concentrations around 1.5 mg/ml (see Table 3). At 0.5 mg/ml this difference increased to 1600-fold. The aggregation of both proteins showed a concentration dependence. The higher the concentration the higher the levels of aggregation that were seen.

5. Comparison of 212 and 218 Linkers in vivo

Both the observation that longer linkers result in less aggregation and that linkers could be proteolytically susceptible have possible implications in the in vivo therapeutic applications of sFv polypeptides, as well as other linked fusion polypeptides. First, aggregation could result in the unwanted accumulation of sFv in non-target tissues. Second, the proteolysis of a sFv to an Fv is likely to result in a loss of affinity. These two effects were examined in vivo in a human tumor model system. We examined the in vivo performance of the CC49/212 and CC49/218 sFvs in an LS-174T tumor xenograft in athymic nude mice.

Female athymic nude mice (nu/nu), obtained from Charles River (Wilmington, Mass.) at 4–6 weeks of age, were injected subcutaneously on the back with $1 \times 10^6$ LS-174T human colon carcinoma cells under a NIH-approved protocol (Tom, R. H., et al., *In Vitro (Rockville)* 12:180–191 (1976)). Animals were used in biodistribution studies when the animals' tumors measured 0.5 to 0.8 cm in diameter, approximately two weeks later. Dual-label studies were performed with tumor-bearing mice injected via the tail vein with approximately $2–10 \times 10^6$ cpm of each labeled CC49 sFv. Mice (3–4/data point) were killed at various time points by exsanguination. The blood, tumor and all the major organs were collected, wet-weighed and counted in a gamma scintillation counter. The % injected dose per gm (% ID/g) and radiolocalization index (% ID/g in the tumor divided by the % ID/g in normal tissue) for each were determined.

The biodistribution of tile $^{177}Lu$ labeled CC49/212 and CC49/218 sFv polypeptides was determined at various times in athymic nude mice bearing the two-week old human colon carcinomas. Of the six tissues examined, three tissues showed significant differences between the CC49/212 and CC49/218 sFvs (see Table 4). The spleen and the liver showed three- to four-fold higher accumulations of the CC49/212 sFv compared to the CC49/218 sFv. At the 24 and 48 hour time points the CC49/212 sFv showed a 60% higher accumulation at the tumor. The other three tissues (blood, kidney and lung) show little or no differences.

The higher level of CC49/212 sFv accumulation in the spleen and liver is likely due to the higher degree of aggregation of tile sample injected. Both the spleen and liver metabolize the sFv polypeptides, but due to the higher degree of aggregation of the CC49/212 sFv higher uptake and accumulation of the $^{177}Lu$ radiolabel in these tissues is seen. The higher levels of CC49/212 sFv in the tumor at later times may be due to the increased avidity of the aggregates. The very high levels of accumulation of both sFv polypeptides in the kidneys probably reflects the catabolism of the protein in the kidneys, with subsequent retention of the $^{177}$Lu Schott et al., Cancer Res. 52:6413–6417,1992).

TABLE 3

Aggregation Rates of the CC49/212 and CC49/218 sFvs

| Protein | Concentration (mg/ml) | Rate of Aggregation (%/hr) | (%/day) |
|---|---|---|---|
| CC49/212 | 1.89 | 0.732 | 17.56 |
|  | 0.49 | 0.120 | 2.88 |
| CC49/218 | 1.49 | 0.0092 | 0.221 |
|  | 0.62 | 0.00008 | 0.0018 |

TABLE 4

Biodistribution of the $^{177}$Lu labeled CC49/212 and CC49/218 sFvs

|  |  | % ID / gm | | | |
|---|---|---|---|---|---|
| Organ | Liver | 1 h | 6 h | 24 h | 48 h |
| Tumor | 212 | 2.4 | 2.0 | 2.2 | 1.6 |
|  | 218 | 2.6 | 1.9 | 1.4 | 1.0 |
|  | 212/218 ratio | 0.9 | 1.0 | 1.6 | 1.6 |
| Blood | 212 | 1.8 | 0.2 | <0.1 | <0.1 |
|  | 218 | 0.9 | 0.2 | <0.1 | <0.1 |
|  | 212/218 ratio | 2.0 | 1.0 | — | — |
| Liver | 212 | 7.4 | 9.4 | 5.5 | 4.0 |
|  | 218 | 3.1 | 2.3 | 1.8 | 1.1 |
|  | 212/218 ratio | 2.4 | 4.1 | 3.1 | 3.6 |
| Spleen | 212 | 9.6 | 7.0 | 7.2 | 6.8 |
|  | 218 | 3.1 | 2.1 | 1.9 | 1.6 |
|  | 212/218 ratio | 3.1 | 3.3 | 3.8 | 4.2 |
| Kidney | 212 | 241.1 | 219.1 | 197.6 | 156.1 |
|  | 218 | 303.9 | 266.0 | 222.9 | 161.5 |
|  | 212/218 ratio | 0.8 | 0.8 | 0.9 | 1.0 |
| Lung | 212 | 1.7 | 0.8 | 0.7 | 0.5 |
|  | 218 | 1.3 | 1.0 | 0.6 | 0.5 |
|  | 212/218 ratio | 1.3 | 0.8 | 1.2 | 1.0 |

6. Construction, Purification, and Testing of 4-4-20/CC49 Heterodimer $F_v$

The goals of this experiment were to produce, purify and analyze for activity a new heterodimer Fv that would bind to both fluorescein and the pan-carcinoma antigen TAG-72. The design consisted of two polypeptide chains, which associated to form the active heterodimer Fv. Reports of some of this work have appeared in the scientific literature (Essig et al., *J. Mol. Biol.* 234:897–901 (1993) and Whitlow et al., *Protein Engineering* 6(8):989–995 (1993)). Each polypeptide chain can be described as a mixed single-chain Fv (mixed sFv). The first mixed sFv (GX 8952) comprised a 4-4-20 variable light chain ($V_L$) and a CC49 variable heavy chain ($V_H$) connected by a 217 polypeptide linker (FIG. 3). The second mixed sFv (GX 8953) comprised a CC49 $V_L$ and a 4-4-20 $V_H$ connected by a 217 polypeptide linker (FIG. 4). The sequence of the 217 polypeptide linker is shown in Table 2.

Results
A. Purification
One 10-liter fermentation of the *E. coli* production strain for each mixed sFv was grown on casein digest-glucose-salts medium at 32° C. to an optical density at 600 nm of 15 to 20. The mixed sFv expression was induced by raising the temperature of the fermentation to 42° C. for one hour. 277 gm (wet cell weight) of *E. coli* GX 8952 and 233 gm (wet cell weight) of *E. coli* GX 8953 were harvested in a centrifuge at 7000 g for 10 minutes. The cell pellets were kept and the supernate discarded. The cell pellets were frozen at −20° C. for storage.

2.55 liters of lysis/wash buffer (50 mM Tris/200 mM NaCl/1 mM EDTA, pH 8.0) was added to both of the mixed sFv's cell pellets, which were previously thawed and combined to give 510 gm of total wet cell weight. After complete suspension of the cells they were then passed through a Gaulin homogenizer at 9000 psi and 4° C. After this first pass the temperature increased to 23° C. The temperature was immediately brought down to 0° C. using dry ice and methanol. The cell suspension was passed through the Gaulin homogenizer a second time and centrifuged at 8000 rpm with a Dupont GS-3 rotor for 60 minutes. The supernatant was discarded after centrifugation and the pellets resuspended in 2.5 liters of lysis/wash buffer at 4° C. This suspension was centrifuged for 45 minutes at 8000 rpm with the Dupont GS-3 rotor. The supernatant was again discarded and the pellet weighed. The pellet weight was 136.1 gm.

1300 ml of 6M Guanidine Hydrochloride/50 mM Tris/50 mM KCl/10 mM CaCl$_2$pH 8.0 at 4° C. was added to the washed pellet. An overhead mixer was used to speed solubilization. After one hour of mixing, the heterodimer GuHCl extract was centrifuged for 45 minutes at 8000 rpm and the pellet was discarded. The 1425 ml of lieterodimer Fv 6M GuHCl extract was slowly added (16 ml/min) to 14.1 liters of Refold Buffer (50 mM Tris/50 mM KCl/10 mM CaCl$_2$, pH 8.0) under constant mixing at 4° C. to give an approximate dilution of 1:10. Refolding took place overnight at 4° C.

After 17 hours of refolding the anti-fluorescein activity was checked by a 40% quenching assay, and the amount of active protein calculated. 150 mg total active heterodimer Fv was found by the 40% quench assay, assuming a 54,000 molecular weight.

4 liters of prechilled (4° C.) 190 proof ethanol was added to the 15 liters of refolded heterodimer with mixing for 3 hours. The mixture sat overnight at 4° C. A flocculent precipitate had settled to the bottom after this overnight treatment. The nearly clear solution was filtered through a Millipak-200 (0.22$\mu$) filter so as to not disturb the precipitate. A 40% quench assay showed that 10% of the anti-fluorescein activity was recovered in the filtrate.

The filtered sample of heterodimer was dialyzed, using a Pellicon system containing 10,000 dalton MWCO membranes, with dialysis buffer (40 mM MOPS/0.5 mM CaAcetate, pH 6.4) at 4° C. 20 liters of dialysis buffer was required before the conductivity of the retentate was equal to that of the dialysis buffer (~500 $\mu$S). After dialysis the heterodimer sample was filtered through a Millipak-20 filter, 0.22$\mu$. After this step a 40% quench assay showed there was 8.8 mg of active protein.

The crude heterodimer sample was loaded on a Poly CAT A cation exchange column at 20 ml/min. The column was previously equilibrated with 60 mM MOPS, 1 mM Calcium Acetate (CaAc) pH 6.4, at 4° C., (Buffer A). After loading, the column was washed with 150 ml of Buffer A at 15 ml/min. A 50 min linear gradient was performed at 15 ml/min using Buffer A and Buffer B (60 mM MOPS, 20 mM CaAc pH 7.5 at 4° C.). The gradient conditions are presented in Table 5. Buffer C comprises 60 mM MOPS, 100 mM CaCl$_2$, pH 7.5.

TABLE 5

| Time | % A | % B | % C | Flow |
|---|---|---|---|---|
| 0:00 | 100.0 | 0.0 | 0.0 | 15 ml/min |
| 50:00 | 0.0 | 100.0 | 0.0 | 15 ml/min |
| 52:00 | 0.0 | 100.0 | 0.0 | 15 ml/min |
| 54:00 | 0.0 | 0.0 | 100.0 | 15 ml/min |
| 58:00 | 0.0 | 0.0 | 100.0 | 15 ml/min |
| 60:00 | 100.0 | 0.0 | 0.0 | 15 ml/min |

Figure 5:
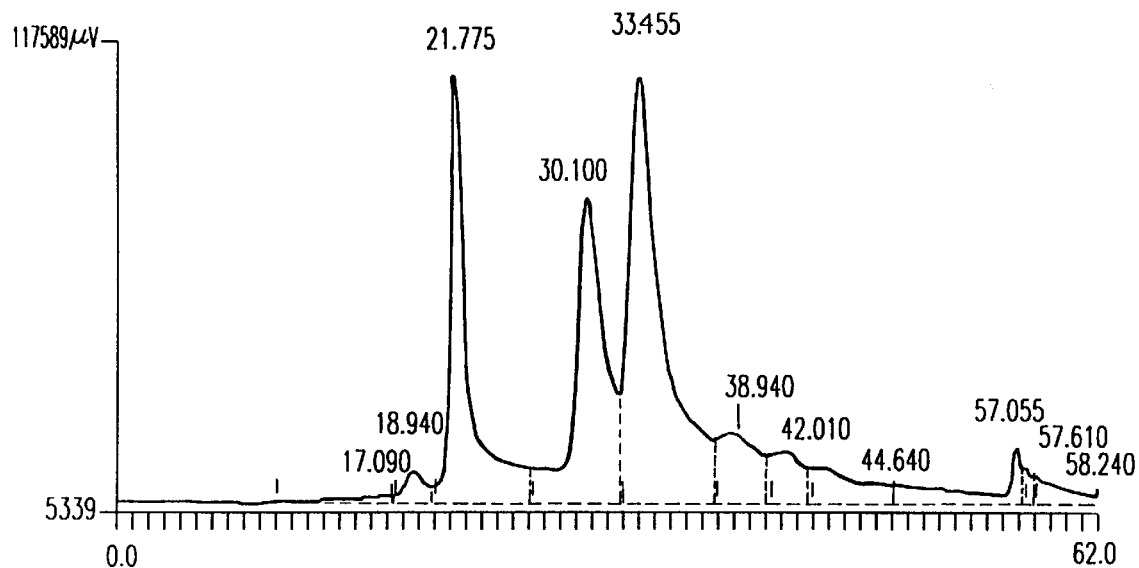
FIG. 5 is a chromatogram depicting the purification of CC49/4-4-20 heterodimer Fv on a cation exchange high performance liquid chromatographic column. The column is a PolyCAT A aspartic acid column (Poly LC, Columbia, Md.). The heterodimer Fv is shown as peak 5, eluting at 30.10 min.

Approximately 50 ml fractions were collected and analyzed for activity, purity, and molecular weight by size-exclusion chromatography. The fractions were not collected by peaks, so contamination between peaks is likely. Fractions 3 through 7 were pooled (total volume ~218 ml), concentrated to 50 ml and dialyzed against 4 liters of 60 mM MOPS, 0.5 mM CaAc pH 6.4 at 4° C. overnight. The dialyzed pool was filtered through a 0.22μ filter and checked for absorbance at 280 nm. The filtrate was loaded onto the PolyCAT A column, equilibrated with 60 mM MOPS, 1 mM CaAc pH 6.4 at 4° C., at a flow rate of 10 ml/min. Buffer B was changed to 60 mM MOPS, 10 mM CaAc pH 7.5 at 4° C. The gradient was run as in Table 5. The fractions were collected by peak and analyzed for activity, purity, and molecular weight. The chromatogram is shown in FIG. 5. Fraction identification and analysis is presented in Table 6.

TABLE 6

Fraction Analysis of the Heterodimer Fv protein

| Fraction No. | $A_{280}$ reading | Total Volume (ml) | HPLE-SE Elution Time (min) |
|---|---|---|---|
| 2 | 0.161 | 36 | 20.525 |
| 3 | 0.067 | 40 | |
| 4 | 0.033 | 40 | |
| 5 | 0.178 | 45 | 19.133 |
| 6 | 0.234 | 50 | 19.163 |
| 7 | 0.069 | 50 | |
| 8 | 0.055 | 40 | |

Figure 6:
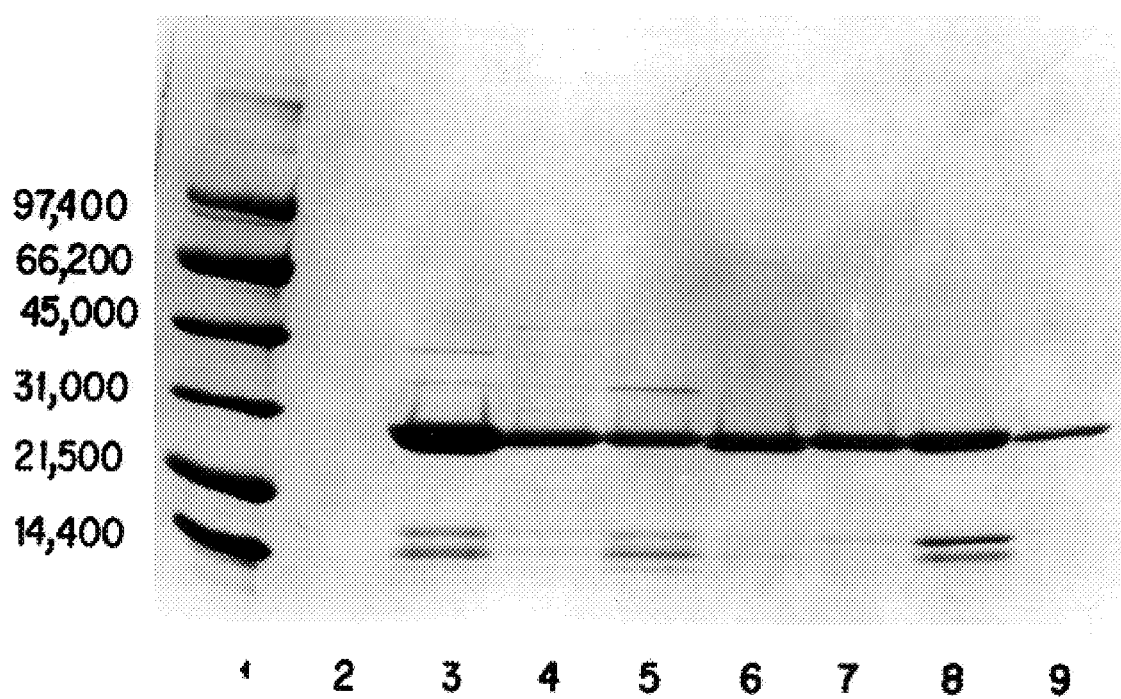
FIG. 6 is a coomassie-blue stained 4–20% SDS-PAGE gel showing the proteins separated in FIG. 5. Lane 1 contains the molecular weight standards. Lane 3 contains the starting material before separation. Lanes 4–8 contain fractions 2, 3, 5, 6 and 7, respectively. Lane 9 contains purified CC49/212.

Fractions 2 to 7 and the starting material were analyzed by SDS gel electrophoresis, 4–20%. A picture and description of the gel is presented in FIG. 6.

B. HPLC size exclusion result

Figure 7:
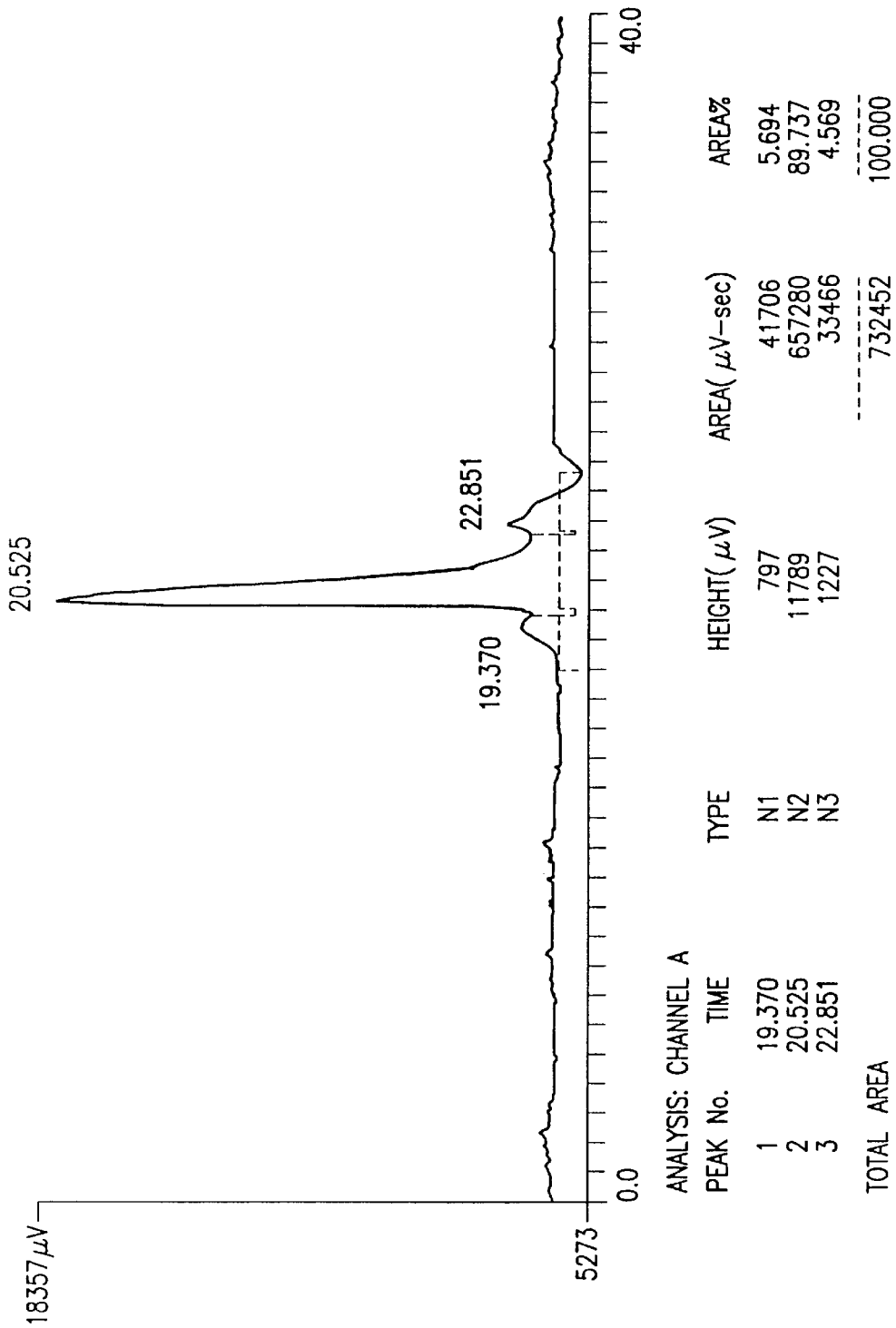
FIG. 7 is a chromatogram used to determine the molecular size of fraction 2 from FIG. 5. A TSK G3000SW gel filtration HPLC column was used (Toyo Soda, Tokyo, Japan).
Figure 8:
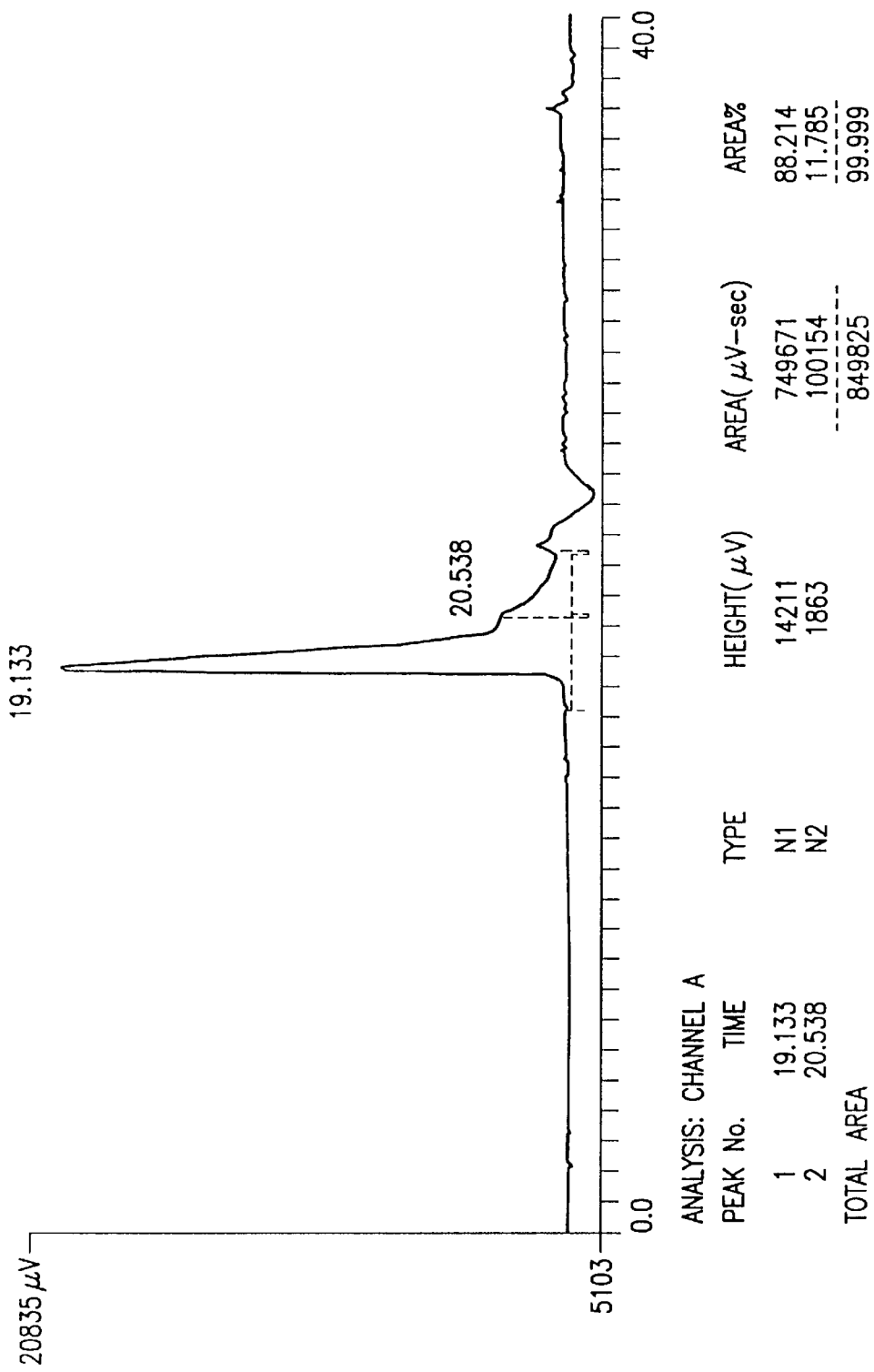
FIG. 8 is a chromatogram used to determine the molecular size of fraction 5 from FIG. 5. A TSK G3000SW gel filtration HPLC column was used (Toyo Soda, Tokyo, Japan).
Figure 9:
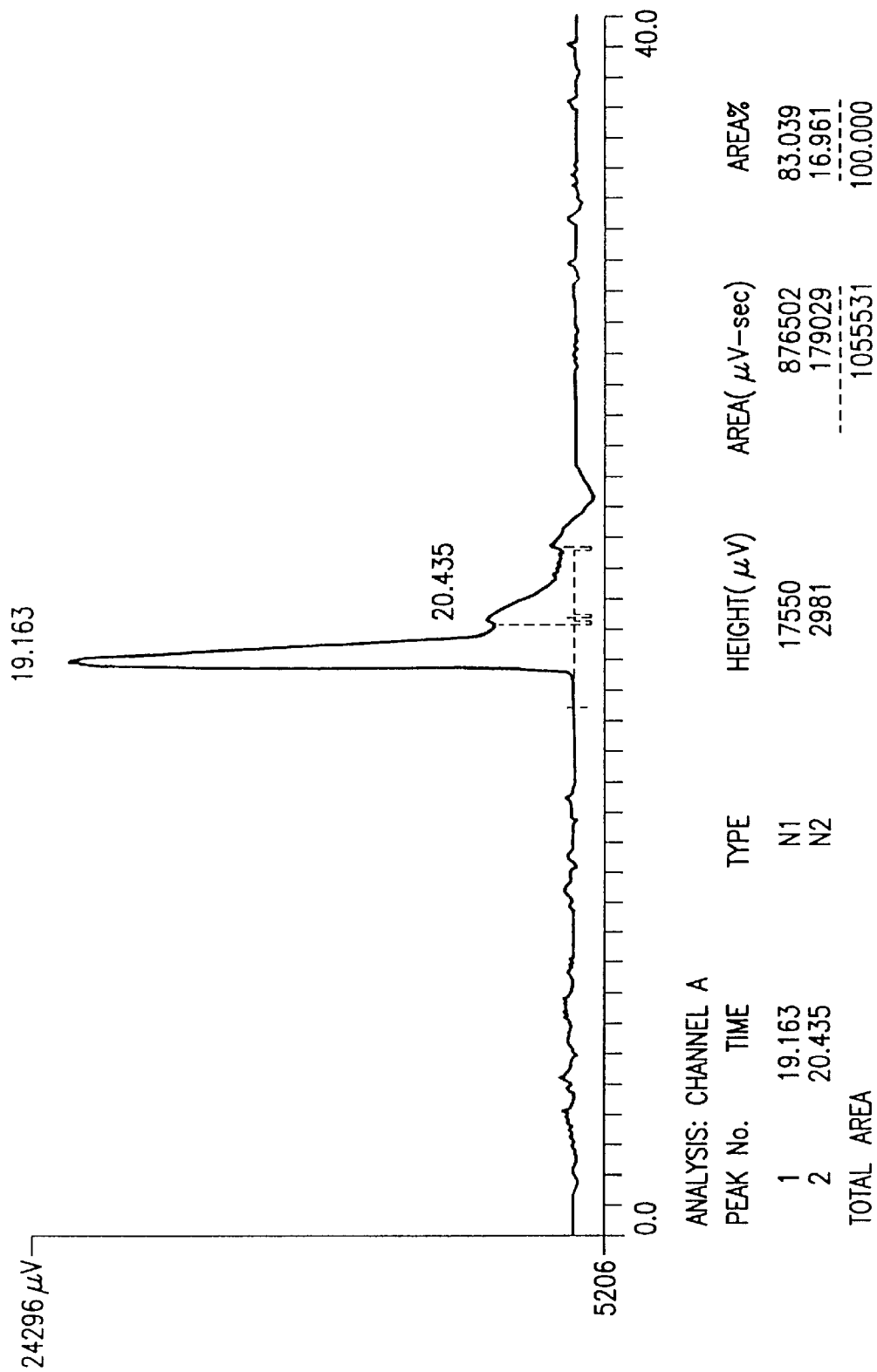
FIG. 9 is a chromatogram used to determine the molecular size of fraction 6 from FIG. 5. A TSK G3000SW gel filtration HPLC column was used (Toyo Soda, Tokyo, Japan).

Fractions 2, 5, and 6 correspond to the three main peaks in FIG. 5 and therefore were chosen to be analyzed by HPLC size exclusion. Fraction 2 corresponds to the peak that runs at 21.775 minutes in the preparative purification (FIG. 5), and runs on the HPLC sizing column at 20.525 minutes, which is in the monomeric position (FIG. 7). Fractions 5 and 6 (30.1 and 33.455 minutes, respectively, in FIG. 5) run on the HPLC sizing column (FIGS. 8 and 9) at 19.133 and 19.163 minutes, respectively (see Table 6). Therefore, both of these peaks could be considered dimers. 40% Quenching assays were performed on all fractions of this purification. Only fraction 5 gave significant activity. 2.4 mg of active CC49/4-4-20 heterodimer Fv was recovered in fraction 5, based on the Scatchard analysis described below.

C. N-terminal sequencing of the fractions

The active heterodimer Fv faction should contain both polypeptide chains. Internal sequence analysis showed that fractions 5 and 6 displayed N-terminal sequences consistent with the presence of both the Gx8952 and Gx8953 polypeptides and fraction 2 displayed a single sequence corresponding to the Gx8953 polypeptide only. We believe that fraction 6 was contaminated by fraction 5 (see FIG. 5) since only fraction 5 had significant activity.

D. Anti-fluorescein activity by Scatchard analysis

Figure 10:
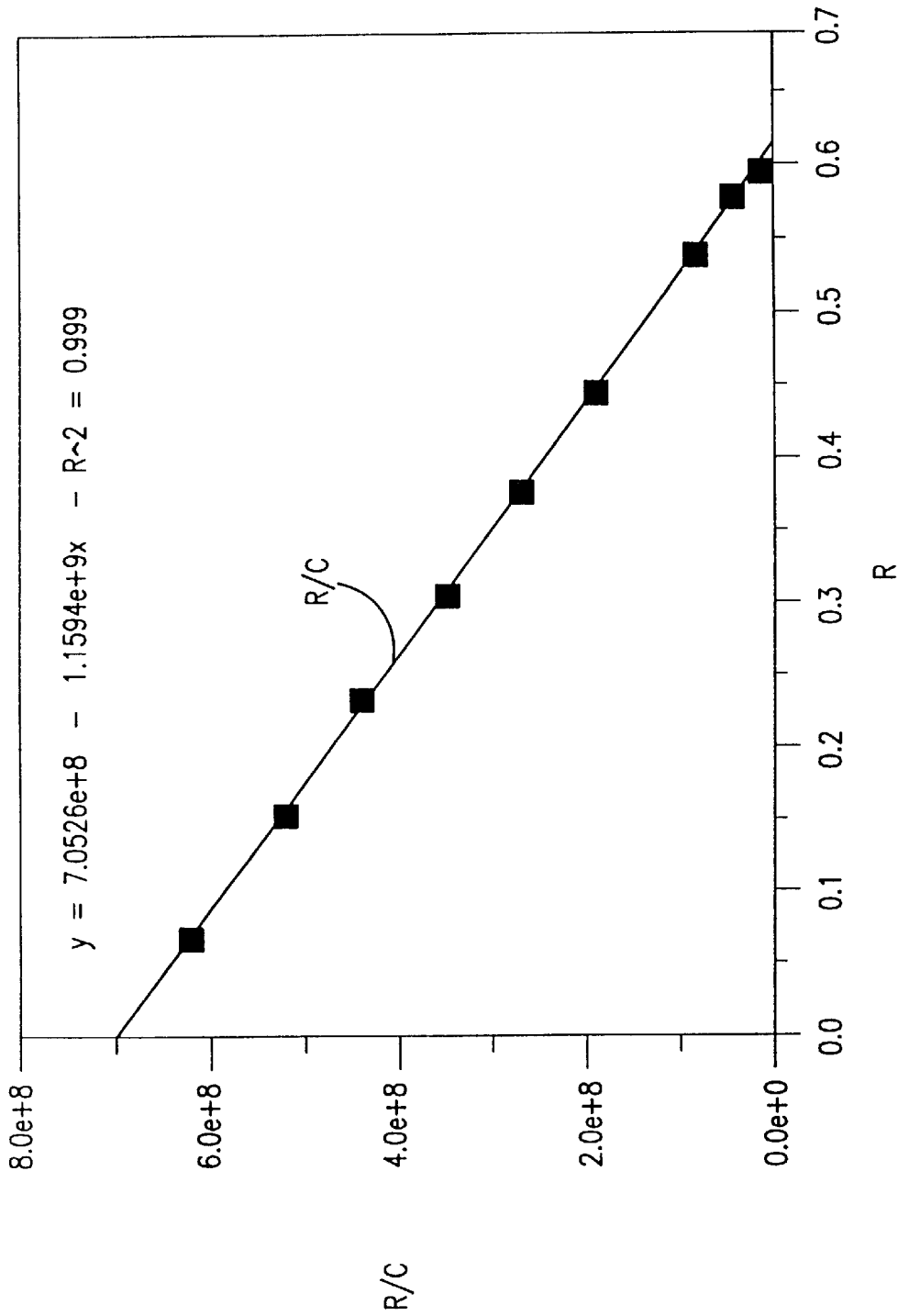
FIG. 10 shows a Scatchard analysis of the fluorescein binding affinity of the CC49/4-4-20 heterodimer Fv (fraction 5 in FIG. 5).

The fluorescein association constants (Ka) were determined for fractions 5 and 6 using the fluorescence quenching assay described by Herron, J. N., in *Fluorescence Hapten: An Immunological Probe*, E. W. Voss, ed., CRC Press, Boca Raton, Fla. (1984). Each sample was diluted to approximately $5.0 \times 10^{-8}$ M with 20 mM HEPES buffer pH 8.0. 590 μl of the $5.0 \times 10^{-8}$ M sample was added to a cuvette in a fluorescence spectrophotometer equilibrated at room temperature. In a second cuvette 590 μl of 20 mM HEPES buffer pH 8.0 was added. To each cuvette was added 10 μl of $3.0 \times 10^{-7}$ M fluorescein in 20 mM HEPES buffer pH 8.0, and the fluorescence recorded. This is repeated until 140 μl of fluorescein had been added. The resulting Scatchard analysis for fraction 5 shows a binding constant of $1.16 \times 10^9$ $M^{-1}$ for fraction #5 (see FIG. 10). This is very close to the 4-4-20/212 sFv constant of $1.1 \times 10^9$ $M^{-1}$ (see Pantolianio et al., *Biochemistry* 30:10117–10125 (1991)). The R intercept on the Scatchard analysis represents the fraction of active material. For fraction 5, 61% of the material was active. The graph of the Scatchard analysis on fraction 6 shows a binding constant of $3.3 \times 10^8$ $M^{-1}$ and 14% active. The activity that is present in fraction 6 is most likely contaminations from fraction 5.

E. Anti-TAG-72 activity by competition ELISA

The CC49 monoclonal antibody was developed by Dr. Jeffrey Schlom's group, Laboratory of Tumor Immunology and Biology, National Cancer Institute. It binds specifically to the pan-carcinoma tumor antigen TAG-72. See Muraro, R., et al., *Cancer Research* 48:4588–4596 (1988).

Figure 11:
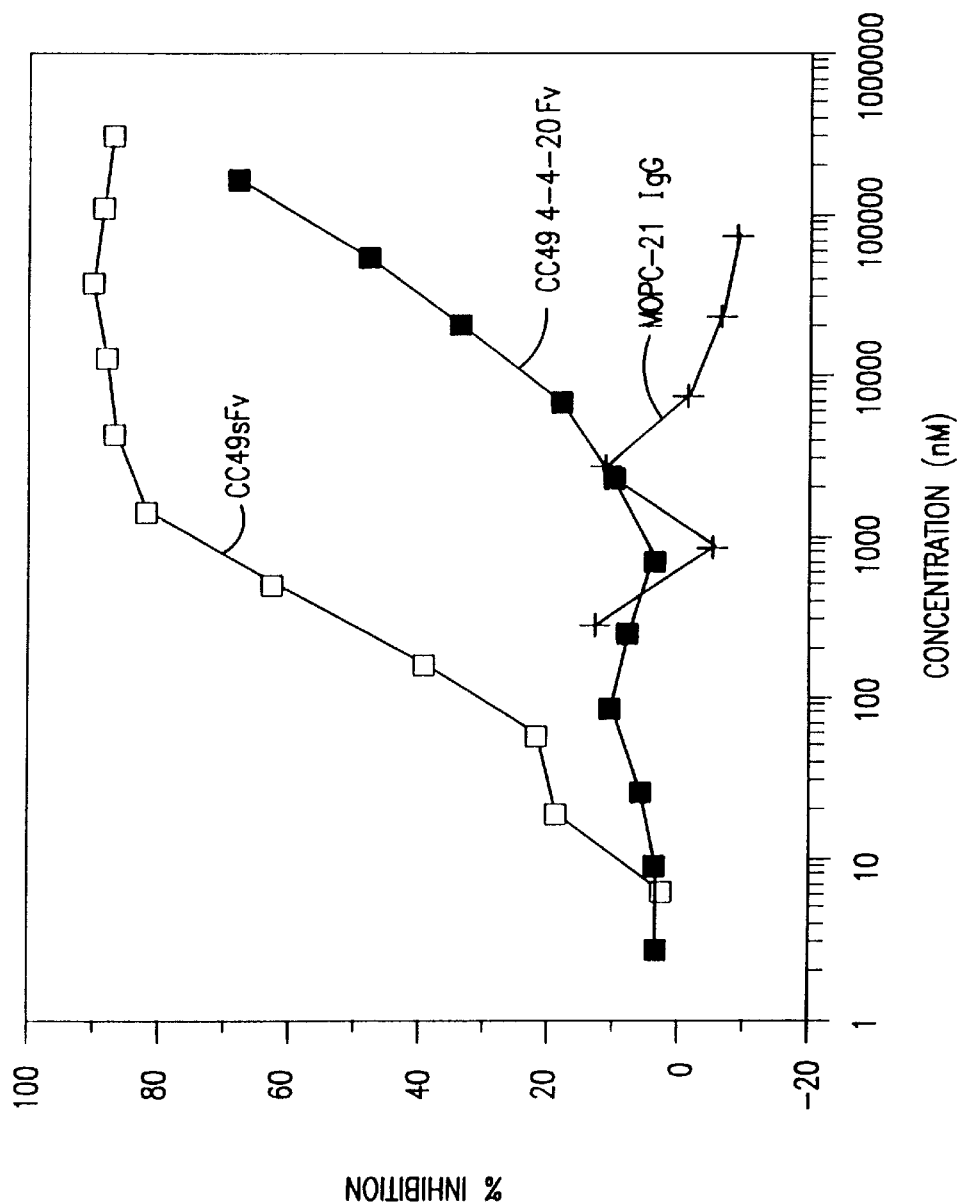
FIG. 11 is a graphical representation of three competition enzyme-linked immunosorbent assays (ELISA) in which unlabeled CC49/4-4-20 Fv (closed squares) CC49/212 single-chain Fv (open squares) and MOPC-21 IgG (+) competed against a biotin-labeled CC49 IgG for binding to the TAG-72 antigen on a human breast carcinoma extract. MOPC-2 1 is a control antibody that does not bind to the TAG-72 antigen.

To determine the binding properties of the bivalent CC49/4-4-20 Fv (fraction 5) and the CC49/212 sFv, a competition enzyme-linked immunosorbent assay (ELISA) was set up in which a CC49 IgG labeled with biotin was competed against unlabeled CC49/4-4-20 Fv and the CC49/212 sFv for binding to TAG-72 on bovine submaxillary mucin (see FIG. 11). One μg of bovine submaxillary mucin (Sigma, St. Louis, Mo.) in 50 ml of PBS was adsorbed overnight at 37° C. to each well of a microtiter plate, and then blocked with 100 μl of 5% bovine serum albumin (BSA) at 37° C. Samples were diluted in 1% BSA in phosphate buffered saline (PBS) from a starting concentration of 10 μg/25 μl/well. To each well 100 ng of biotinylated CC49 IgG in 25 μl of PBS was added. The wells were covered and incubated overnight at 4° C. After washing and aspirating the wells three times with 1% BSA in PBS, 50 μl of the Avidin/Biotin complex (ABC Vector, Vectastain Kit) was added to each well and incubated for one hour at 37° C. The wells were washed and aspirated three times with 1% BSA in PBS. One hundred μl of the ELISA buffer was added to each well and incubated for 10 min in the dark at room temperature. The reaction was stopped by tile addition of 25 μl of 4M ammonium sulfate. The optical density was read at 490 nm. This competition ELISA showed that the bivalent CC49 4-4-20 Fv binds to the TAG-72 antigen. The bivalent CC49/4-4-20 Fv needed a two hundred-fold higher protein concentration to displace the IgG than the CC49/212 single-chain Fv.

7. Construction, Purification And Characterization of A33/218 Single Chain Fv

The goal of this experiment was to produce a new single chain Fv. The Fv domain has been selected from the monoclonal antibody known in the literature as A33 (Welt, S. et al., *J. Clin. Oncology* 8:1894–1906 (1990), Welt, S. et al., U.S. Pat. No. 5,160,723). The sFv (GX9452/pGX9451) comprised an A33 variable light chain ($V_L$) and an A33 variable heavy chain ($V_H$) connected by a 218 polypeptide linker [SEQ ID No. 15]. The sequence of the 218 polypeptide linker is shown in Table 2.

A. Cloning and Genetic Construction

Plasmid pGX8910 contains the completed A33/212 gene and was used as the starting template for the A33/218 version. A PCR strategy was utilized where two PCR amplifications of the $V_L$ and $V_H$ segments of the genes were performed with primers which included the desired 218 linker sequence. These two amplified fragments were joined into a single A33/218 fragment by using a second PCR amplification with splicing-by-overlap extension (Horton et al., *Gene* 77:61–68) to anneal the 218 complementary regions of the two initial fragments and two outside primers to amplify the compete A33/218 gene.

Specifically, primer 3397 (5'-TCTGGTTCTGGTAAACCCGGGAGTG GTGAAGG-TAGCACTAAAGGTGAAGTGAAG -3') [SEQ. ID No. 19]introduces the needed base changes in the 212 linker to create a 218 linker sequence. When primer 3397 was used with the downstream flanking primer 3250 in a PCR amplification, the 218/$V_H$ A33 segment was generated. A separate PCR amplification of the $V_L$/218 segment was next done using primers 5004 and 3143. Since primer 5004 (5'-ACCAGAGGTAGAA CCTTTTACTTCCAACTT-3') [SEQ. ID No. 20] has a 5' complementary overlap with primer 3397, a splicing-by-overlap extension based PCR was next accomplished using only the two outside primers from the first two PCR amplifications: primer 3143 (5'-CAGCTATCGCGATTGC-3') [SEQ. ID No. 21] and primer 3250 (5'-GAGTTCTGAGGTCATTACTG-3') [SEQ. ID No. 22]. This produced a completed A33/218 gene fragment.

In order to ligate this PCR fragment into the OL/PR expression vector which was used in the starting pGX8910 vector, the fragment was digested with AatII plus HindIII which produced a A33 $V_L$/218 segment which was ligated into plasmid pGX8910 which had been digested also with AatII plus HindIII. There are two HindIII sites in pGX8910: one site is at the 218 junction to $V_H$ and a second site is just downstream of the $V_H$. Hence, in the initial ligation of the AatII-HindIII fragments described above, the resulting plasmid has only the $V_L$/218 insert. This plasmid was then digested with HindIII and the purified A33 $V_H$ segment from the initial HindIII digestion was re-ligated back into the vector to produce the completed A33/218 expression vector construction. DNA sequence analysis using sequencing primer 3398 (5'-GATTTCACTCTCACCATTAG-3') [SEQ. ID No. 22] on the double-stranded plasmid confirmed the $V_L$/218/$V_H$ junction sequences.

This plasmid was transformed into GX6712 and heat-induced expression of a 26 kd protein was observed using our standard expression protocol for our OL/PR based vectors. This expression strain/plasmid was subsequently designated GX9452/pGX9451.

B. Purification

One 10-liter fermentation of the *E. Coli* production strain (GX9452) is grown on Casein digest-glucose-salts medium at 32° C. to an optical density at 600 nm of 15 to 20. The A33/218 sFv expression is induced by raising the temperature of the fermentation to 42° C. for one to two hours. The cells are harvested in a centrifuge at 7000 g for 10 minutes. Tile cell pellets are kept and the supernate discarded. The cell pellets are normally frozen at -20 °C. for storage prior to purification.

The purification of the sFv's has been previously described by Pantoliano et al. *Biochemistry* 30:10117–10125 (1991) and Whitlow and Filpula, *Methods* 2:97–105 (1991). The A33/218 sFv is purified with a minor procedural modification, in which the initial cation exchange HPLC step, using the RCM Waters Accell Plus CM ion exchange column, is omitted.

C. Characterization of the A33/218 sFv

The A33/218 sFv is compared to the A33/212 sFv for aggregation rates, proteolytic susceptibility and activity.

1. Proteolytic Susceptibility $1.0 \times 10^5$M A33/212 and A33/218 sFv's is treated with $2.5 \times 10^{-9}$M subtilisin BPN' (Type XXVII protease, Sigma, St. Louis, Mo.) or $7.7 \times 10^{-9}$M trypsin at 37° C. At various times the proteolytic digestion is stopped with the addition of 2 $\mu$l of 0.1M PMSF solution to a 200 $\mu$l sample. The percent intact sFv remaining is monitored by reverse phase HPLC at 60° C. A linear gradient of 5% to 70% acetonitrile, 0.1% TFA is run on a Waters HPLC system with a PLRP-S column (Polymer Labs., Church Stretton, England) in a heating unit (Timberline Instruments, Boulder, Colo.), following the procedures of Nugent (1990). The data are collected on a MacIntosh SE (Apple Computer, Cupertino, Calif.) running the Dynamac software package (Rainin Instrument Co., Woburn, Mass.). The half-life ($t_{1/2}$) is determined from a semilog plot of the fraction of intact A33 sFv remaining versus time using SigmaPlot 4.1 (Jandel Scientific, San Refael, Calif.).

2. Aggregation Rates

Gel filtration HPLC chromatography is used to quantitate the degree of aggregation for the A33/218 sFvs. 10 to 50 $\mu$l samples are injected onto a Waters HPLC system equipped with a 7.8 mm×300 mm TSK G3000SW column (Toso Haas, Tokyo Japan). The column is equilibrated and the samples are eluted using 50 mM MOPS, 100 mM NaCl buffer, pH 7.5, at a flow rate of 0.5 ml/min. The data are collected on a Macintosh SE (Apple Computer, Cupertino, Calif.) running tile Dynamax software package (Rainin Instrument Co., Woburn, Mass.).

Conclusions

We have produced a heterodimer Fv from two complementary mixed sFv's which has been shown to have the size of a dimer of the sFv's. The N-terminal analysis has shown that the active heterodimer Fv contains two polypeptide chains. The heterodimer Fv has been shown to be active for both fluorescein and TAG-72 binding.

All references mentioned herein are incorporated by reference into this disclosure.

Having now fully described the invention by way of illustration and example for purposes of clarity and understanding, it will be apparent to those of ordinary skill in the art that certain changes and modifications may be practiced within the scope of the invention, as limited only by the following claims.

We claim:

1. A DNA molecule encoding a linked fusion polypeptide comprising a first polypeptide and a second polypeptide connected by a peptide linker, wherein said peptide linker is 18 to 50 amino acid residues long, said peptide linker comprises one or more occurrences of the sequence XP wherein X is a charged amino acid, and said peptide linker further comprises the sequence represented by GSTSGS-GXPGSGSGEGSTKG (SEQ, ID No. 1), said sequence positioned within said peptide linker so as to inhibit proteolysis of said linker by either subtilisin or typsin.

2. A DNA molecule encoding the polypeptide comprising the sequence represented by GSTSGSGXPGSGEGSTKG (SEQ. ID No.1) wherein X is a charged amino acid.

3. The DNA molecule of claim 1 wherein said first and second polypeptides are not derived from the same single chain protein or from the same chain of a multi-chain protein.

4. The DNA molecule of claim 3 wherein said first and second polypeptides are derived from different proteins.

5. The DNA molecule of claim 4 wherein said first and second polypeptides are derived from members of the immunoglobulin superfamily.

6. The DNA molecule of claim 5 wherein said first and second polypeptides are derived from immunoglobulins.

7. The DNA molecule of claim 6 wherein said linked fusion polypeptide is a mixed sFv.

8. The DNA molecule of claim 1 wherein said first and second polypeptides are derived from the same multi-chain protein.

9. The DNA molecule of claim 8 wherein said multi-chain protein is a member of the immunoglobulin superfamily.

10. The DNA molecule of claim 9 wherein said multi-chain protein is a T cell receptor.

11. The DNA molecule of claim 9 wherein said multi-chain protein is an immunoglobulin.

12. The DNA molecule claim 11 wherein said first polypeptide comprises the binding portion of the variable region of the heavy or light chain of said immunoglobulin.

13. The DNA molecule of claim 11 wherein said second polypeptide comprises the binding portion of the variable region of the heavy or light chain of said immunoglobulin.

14. The DNA molecule of claim 11 wherein said first polypeptide comprises the binding portion of the variable region of the heavy chain of said immunoglobulin and said second polypeptide comprises the binding portion of the variable region of the light chain of said immunoglobulin.

15. The DNA molecule of claim 1 wherein said peptide linker comprises about 18 to about 30 amino acids.

16. The DNA molecule of claim 1 wherein said sequence XP occurs at positions 8 and 9 from the amino terminus of said peptide linker.

17. The DNA molecule of claim 1 wherein said charged amino acid is a positively-charged amino acid.

18. The DNA molecule of claim 17 wherein said charged amino acid is lysine or arginine.

19. The DNA molecule of claim 1 wherein X is lysine or arginine.

20. A DNA molecule encoding a linked fusion polypeptide comprising a first polypeptide and a second polypeptide connected by a peptide linker, wherein said first and second polypeptides are derived from the same multi-chain protein, said multi-chain protein being a member of the immunoglobulin superfamily; and said peptide linker comprising one or more occurrences of the sequence XP, wherein X is a charged amino acid and said peptide linker sequence comprises at least one sequence selected from the group of sequences consisting of sequence represented by GTSGS-GXPSGEGSTKG (SEQ. ID No. 1), GTSGSGXPSGEG-STKG (SEQ. ID No. 10). GSTSGKSEGKG (amino acid nos. 113–124 of SEQ. ID No. 12), and GSTSGXPSEGKG (SEQ. ID NO 25), said peptide linker sequence being positioned within said peptide linker so as to inhibit proteolysis of said linker by either subtilisin or trypsin.

21. The DNA molecule of claim 20 wherein said multi-chain protein is an immunoglobulin.

22. The DNA molecule of claim 21 wherein said first polypeptide comprises the binding portion of the variable region of the heavy or light chain of said immunoglobulin.

23. The DNA molecule of claim 21 wherein said second polypeptide comprises the binding portion of the variable region of the heavy or light chain of said immunoglobulin.

24. The DNA molecule of claim 21 wherein said first polypeptide comprises the binding portion of the variable region of the heavy chain of said immunoglobulin and said second polypeptide comprises the binding portion of the variable region of the light chain of said immunoglobulin.

25. The DNA molecule of claim 1 wherein said first polypeptide is CC49 $V_L$ and said second polypeptide is CC49 $V_H$.

26. The DNA molecule of claim 1 wherein said first polypeptide is A33 $V_L$ and said second polypeptide is A33 $V_H$.

27. A DNA molecule encoding a linked fusion polypeptide comprising a first polypeptide and a second polypeptide connected by a peptide linker, wherein said peptide linker is 18 to 50 amino acid residues long, said peptide linker comprises one or more occurrences of a sequence XP wherein is a charged amino acid, and said peptide linker further comprises the sequence represented by GSTSGS-GKPGSGEGSTKG (SEQ. ID No. 10), wherein said sequence is positioned within said peptide linker so as to inhibit proteolysis of said linker by either subtilisin or trypsin.

28. The DNA molecule of claim 27 wherein said first polypeptide is 4-4-20 $V_L$ and said second polypeptide is CC49 $V_H$.

29. The DNA molecule of claim 27 wherein said first polypeptide is CC49 $V_L$ and said second polypeptide is 4-4-20 $V_H$.

30. The DNA molecule of claim 27 wherein said first and second polypeptides are not from the same single chain protein or from the same chain of a multi-chain protein.

31. The DNA molecule of claim 30 wherein said first and second polypeptides are from different proteins.

32. The DNA molecule of claim 31 wherein said first and second polypeptides are from members of the immunoglobulin superfamily.

33. The DNA molecule of claim 32 wherein said first and second polypeptides are from immunoglobulins.

34. The DNA molecule of claim 33 wherein said linked fusion polypeptide is a sFv.

35. The DNA molecule of claim 27 wherein said first and second polypeptides are from the same multi-chain protein.

36. The DNA molecule of claim 35 wherein said multi-chain protein is a member of the immunoglobulin superfamily.

37. The DNA molecule of claim 36 wherein said multi-chain protein is a T cell receptor.

38. The DNA molecule of claim 36 wherein said multi-chain protein is an immunoglobulin.

39. The DNA molecule of claim 38 wherein said first polypeptide comprises the binding portion of the variable region of the heavy or light chain of said immunoglobulin.

40. The DNA molecule of claim 38 wherein said second polypeptide comprises the binding portion of the variable region of the heavy or light chain of said immunoglobulin.

41. The DNA molecule of claim 38 wherein said first polypeptide comprises the binding portion of the variable region of the heavy chain of said immunoglobulin and said second polypeptide comprises the binding portion of the variable region of the light chain of said immunoglobulin.

42. The DNA molecule of claim 27 wherein said peptide linker comprises about 18 to about 30 amino acids.

43. The DNA molecule of claim 27 wherein said sequence XP occurs at positions 8 and 9 from the amino terminus of said peptide linker.

44. The DNA molecule of claim 27 wherein said charged amino acid is a positively-charged amino acid.

45. The DNA molecule of claim 44 wherein said charged amino acid is lysine or arginine.

46. A DNA molecule encoding a linked fusion polypeptide comprising a first polypeptide and a second polypeptide connected by a peptide linker, wherein said peptide linker is 12 to 50 amino acid residues long, said peptide linker comprises one or more occurrences of a sequence XP wherein X is a charged amino acid, and said peptide linker further comprises the sequence represented by GSTSGKP-SEGKG (amino acid nos. 113–124 of SEQ. ID No. 12), wherein said sequence is positioned within said peptide linker so as to inhibit proteolysis of said linker by at least subtilisin or trypsin.

47. The DNA molecule of claim 46 wherein said first polypeptide is 4-4-20 $V_L$ and said second polypeptide is CC49 $V_H$.

48. The DNA molecule of claim 46 wherein said first polypeptide is CC49 $V_L$, said second polypeptide is 4-4-20 $V_H$.

49. The DNA molecule of claim 46 wherein said first and second polypeptides are not derived from the same single chain protein or from the same chain of a multi-chain protein.

50. The DNA molecule of claim 49 wherein said first and second polypeptides are derived from different proteins.

51. The DNA molecule of claim 50 wherein said first and second polypeptides are members of the immunoglobulin superfamily.

52. The DNA molecule of claim 51 wherein said first and second polypeptides are from immunoglobulins.

53. The DNA molecule of claim 52 wherein said linked fusion polypeptide is a sFv.

54. The DNA molecule of claim 46 wherein said first and second polypeptides are from the same multi-chain protein.

55. The DNA molecule of claim 54 wherein said multi-chain protein is a member of the immunoglobulin superfamily.

56. The DNA molecule of claim 55 wherein said multi-chain protein is a T cell receptor.

57. The DNA molecule of claim 55 wherein said multi-chain protein is an immunoglobulin.

58. The DNA molecule claim 57 wherein said first polypeptide comprises the binding portion of the variable region of the heavy or light chain of said immunoglobulin.

59. The DNA molecule of claim 57 wherein said second polypeptide comprises the binding portion of the variable region of the heavy or light chain of said immunoglobulin.

60. The DNA molecule of claim 57 wherein said first polypeptide comprises the binding portion of the variable region of the heavy chain of said immunoglobulin and said second polypeptide comprises the binding portion of the variable region of the light chain of said immunoglobulin.

61. The DNA molecule of claim 46 wherein said peptide linker comprises about 12 to about 30 amino acids.

62. The DNA molecule of claim 46 wherein said sequence XP occurs at positions 6 and 7 from the amino terminus of said peptide linker.

63. The DNA molecule of claim 46 wherein said charged amino acid is a positively-charged amino acid.

64. The DNA molecule of claim 46 wherein said charged amino acid is lysine or arginine.

65. A DNA molecule encoding a linked fusion polypeptide comprising a first polypeptide and a second polypeptide connected by a peptide linker, wherein said peptide linker is 12 to 50 amino acid residues long, said peptide linker comprises one or more occurrences of the sequence XP wherein X is a charged amino acid, and said peptide linker further comprises the sequence represented by GSTSGXP-SEGKG (SEQ. ID NO 25), wherein said sequence is positioned within said peptide linker so as to inhibit proteolysis of said linker by either subtilisin or trypsin.

66. The DNA molecule of claim 65 wherein said first polypeptide is 4-4-20 $V_H$ and said second polypeptide is CC49 $V_H$.

67. The DNA molecule of claim 65 wherein said first polypeptide is CC49 $V_L$, said second polypeptide is 4-4-20 $V_H$.

68. The DNA molecule of claim 65 wherein said fist and second polypeptides are not from the same single chain protein or from the same chain of a multi-chain protein.

69. The DNA molecule of claim 68 wherein said first and second polypeptides are from different proteins.

70. The DNA molecule of claim 69 wherein said first and second polypeptides are from members of the immunoglobulin superfamily.

71. The DNA molecule of claim 70 wherein said first and second polypeptides are from immunoglobulins.

72. The DNA molecule of claim 71 wherein said linked fusion polypeptide is a sFv.

73. The DNA molecule of claim 65 wherein said first and second polypeptides are from the same multi-chain protein.

74. The DNA molecule of claim 73 wherein said multi-chain protein is a member of the immunoglobulin superfamily.

75. The DNA molecule of claim 74 wherein said multi-chain protein is a T cell receptor.

76. The DNA molecule of claim 74 wherein said multi-chain protein is an immunoglobulin.

77. The DNA molecule claim 76 wherein said first polypeptide comprises the binding portion of the variable region of the heavy or light chain of said immunoglobulin.

78. The DNA molecule of claim 77 wherein said second polypeptide comprises the binding portion of the variable region of the heavy or light chain of said immunoglobulin.

79. The DNA molecule of claim 77 wherein said first polypeptide comprises the binding portion of the variable region of the heavy chain of said immunoglobulin and said second polypeptide comprises the binding portion of the variable region of the light chain of said immunoglobulin.

80. The DNA molecule of claim 65 wherein said peptide linker comprises about 12 to about 30 amino acids.

81. The DNA molecule of claim 65 wherein said sequence XP occurs at positions 6 and 7 from the amino terminus of said peptide linker.

82. The DNA molecule of claim 65 wherein said charged amino acid is a positively-charged amino acid.

83. The DNA molecule of claim 82 wherein said charged amino acid is lysine or arginine.

84. A DNA molecule encoding the polypeptide comprising the sequence represented by GSTSGSGKPGSGEGSTKG (SEQ. ID No. 10).

85. A DNA molecule encoding the polypeptide comprising the sequence represented by GSTSGKPSEGKG (amino acid nos. 113–124 of SEQ. ID No. 12).

86. A DNA molecule encoding the polypeptide comprising the sequence represented by GSTSGXPSEGKG (SEQ. ID NO 25) wherein X is a charged amino acid.

* * * * *

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 18 amino acids
        ( B ) TYPE: amino acid
        ( D ) TOPOLOGY: both ( i x ) FEATURE:
        ( A ) NAME/KEY: Peptide
        ( B ) LOCATION: 8
        ( D ) OTHER INFORMATION: /label= Identification
            / note= "The amino acid at position 8 is charged
            and a preferred embodiment of this amino acid is
            lysine or arginine."

( x i ) SEQUENCE DESCRIPTION: SEQ ID NO:1:

Gly Ser Thr Ser Gly Ser Gly Xaa Pro Gly Ser Gly Glu Gly Ser Thr
1               5                   10                  15

Lys Gly ( 2 ) INFORMATION FOR SEQ ID NO:2:

( i ) SEQUENCE CHARACTERISTICS:
        ( A ) LENGTH: 18 amino acids
        ( B ) TYPE: amino acid
        ( D ) TOPOLOGY: both ( x i ) SEQUENCE DESCRIPTION: SEQ ID NO:2:

Lys Glu Ser Gly Ser Val Ser Ser Glu Gln Leu Ala Gln Phe Arg Ser
1               5                   10                  15

Leu Asp ( 2 ) INFORMATION FOR SEQ ID NO:3:

( i ) SEQUENCE CHARACTERISTICS:
        ( A ) LENGTH: 14 amino acids
        ( B ) TYPE: amino acid
        ( D ) TOPOLOGY: both ( x i ) SEQUENCE DESCRIPTION: SEQ ID NO:3:

Val Arg Gly Ser Pro Ala Ile Asn Val Ala Val His Val Phe
1               5                   10

( 2 ) INFORMATION FOR SEQ ID NO:4:

( i ) SEQUENCE CHARACTERISTICS:
        ( A ) LENGTH: 22 amino acids
        ( B ) TYPE: amino acid
        ( D ) TOPOLOGY: both ( x i ) SEQUENCE DESCRIPTION: SEQ ID NO:4:

Ala Gln Gly Thr Leu Ser Pro Ala Asp Lys Thr Asn Val Lys Ala Ala
1               5                   10                  15

Trp Gly Lys Val Met Thr
            20

( 2 ) INFORMATION FOR SEQ ID NO:5:

( i ) SEQUENCE CHARACTERISTICS:
        ( A ) LENGTH: 18 amino acids
        ( B ) TYPE: amino acid
        ( D ) TOPOLOGY: both ( x i ) SEQUENCE DESCRIPTION: SEQ ID NO:5:

Val Glu Gly Gly Ser Gly Gly Ser Gly Gly Ser Gly Gly Ser Gly Gly
1               5                   10                  15

Val Asp ( 2 ) INFORMATION FOR SEQ ID NO:6:

( i ) SEQUENCE CHARACTERISTICS:
        ( A ) LENGTH: 18 amino acids
        ( B ) TYPE: amino acid
        ( D ) TOPOLOGY: both ( x i ) SEQUENCE DESCRIPTION: SEQ ID NO:6:

Gly Ser Ala Ser Ala Pro Lys Leu Glu Glu Gly Glu Phe Ser Glu Ala
1               5                   10                  15

Arg Glu ( 2 ) INFORMATION FOR SEQ ID NO:7:

( i ) SEQUENCE CHARACTERISTICS:
        ( A ) LENGTH: 12 amino acids
        ( B ) TYPE: amino acid
        ( D ) TOPOLOGY: both ( x i ) SEQUENCE DESCRIPTION: SEQ ID NO:7:

Gly Lys Ser Ser Gly Ser Gly Ser Glu Ser Lys Ser
1               5                   10

( 2 ) INFORMATION FOR SEQ ID NO:8:

( i ) SEQUENCE CHARACTERISTICS:
        ( A ) LENGTH: 14 amino acids
        ( B ) TYPE: amino acid
        ( D ) TOPOLOGY: both ( x i ) SEQUENCE DESCRIPTION: SEQ ID NO:8:

Gly Ser Thr Ser Gly Ser Gly Lys Ser Ser Glu Gly Lys Gly
1               5                   10

( 2 ) INFORMATION FOR SEQ ID NO:9:

( i ) SEQUENCE CHARACTERISTICS:
        ( A ) LENGTH: 18 amino acids
        ( B ) TYPE: amino acid
        ( D ) TOPOLOGY: both ( x i ) SEQUENCE DESCRIPTION: SEQ ID NO:9:

Gly Ser Thr Ser Gly Ser Gly Lys Ser Ser Glu Gly Ser Gly Ser Thr
1               5                   10                  15

Lys Gly ( 2 ) INFORMATION FOR SEQ ID NO:10:

( i ) SEQUENCE CHARACTERISTICS:
        ( A ) LENGTH: 18 amino acids
        ( B ) TYPE: amino acid
        ( D ) TOPOLOGY: both ( x i ) SEQUENCE DESCRIPTION: SEQ ID NO:10:

Gly Ser Thr Ser Gly Ser Gly Lys Pro Gly Ser Gly Glu Gly Ser Thr
1               5                   10                  15

Lys Gly ( 2 ) INFORMATION FOR SEQ ID NO:11:

( i ) SEQUENCE CHARACTERISTICS:
        ( A ) LENGTH: 725 base pairs
        ( B ) TYPE: nucleic acid
        ( C ) STRANDEDNESS: both ( D ) TOPOLOGY: both ( i x ) FEATURE:
    ( A ) NAME/KEY: CDS
    ( B ) LOCATION: join(1..714)

( x i ) SEQUENCE DESCRIPTION: SEQ ID NO:11:

| | | | | | | | | | | | | | | | | |
|---|---|---|---|---|---|---|---|---|---|---|---|---|---|---|---|---|
| GAC | GTC | GTT | ATG | ACT | CAG | ACA | CCA | CTA | TCA | CTT | CCT | GTT | AGT | CTA | GGT | 48 |
| Asp | Val | Val | Met | Thr | Gln | Thr | Pro | Leu | Ser | Leu | Pro | Val | Ser | Leu | Gly | |
| 1 | | | | 5 | | | | | 10 | | | | | 15 | | |
| GAT | CAA | GCC | TCC | ATC | TCT | TGC | AGA | TCT | AGT | CAG | AGC | CTT | GTA | CAC | AGT | 96 |
| Asp | Gln | Ala | Ser | Ile | Ser | Cys | Arg | Ser | Ser | Gln | Ser | Leu | Val | His | Ser | |
| | | | 20 | | | | | 25 | | | | | 30 | | | |
| AAT | GGA | AAC | ACC | TAT | TTA | CGT | TGG | TAC | CTG | CAG | AAG | CCA | GGC | CAG | TCT | 144 |
| Asn | Gly | Asn | Thr | Tyr | Leu | Arg | Trp | Tyr | Leu | Gln | Lys | Pro | Gly | Gln | Ser | |
| | | 35 | | | | | 40 | | | | | 45 | | | | |
| CCA | AAG | GTC | CTG | ATC | TAC | AAA | GTT | TCC | AAC | CGA | TTT | TCT | GGG | GTC | CCA | 192 |
| Pro | Lys | Val | Leu | Ile | Tyr | Lys | Val | Ser | Asn | Arg | Phe | Ser | Gly | Val | Pro | |
| | 50 | | | | | 55 | | | | | 60 | | | | | |
| GAC | AGG | TTC | AGT | GGC | AGT | GGA | TCA | GGG | ACA | GAT | TTC | ACA | CTC | AAG | ATC | 240 |
| Asp | Arg | Phe | Ser | Gly | Ser | Gly | Ser | Gly | Thr | Asp | Phe | Thr | Leu | Lys | Ile | |
| 65 | | | | | 70 | | | | | 75 | | | | | 80 | |
| AGC | AGA | GTG | GAG | GCT | GAG | GAT | CTG | GGA | GTT | TAT | TTC | TGC | TCT | CAA | AGT | 288 |
| Ser | Arg | Val | Glu | Ala | Glu | Asp | Leu | Gly | Val | Tyr | Phe | Cys | Ser | Gln | Ser | |
| | | | | 85 | | | | | 90 | | | | | 95 | | |
| ACA | CAT | GTT | CCG | TGG | ACG | TTC | GGT | GGA | GGC | ACC | AAG | CTT | GAA | ATC | AAA | 336 |
| Thr | His | Val | Pro | Trp | Thr | Phe | Gly | Gly | Gly | Thr | Lys | Leu | Glu | Ile | Lys | |
| | | | 100 | | | | | 105 | | | | | 110 | | | |
| GGT | TCT | ACC | TCT | GGT | AAA | CCA | TCT | GAA | GGC | AAA | GGT | CAG | GTT | CAG | CTG | 384 |
| Gly | Ser | Thr | Ser | Gly | Lys | Pro | Ser | Glu | Gly | Lys | Gly | Gln | Val | Gln | Leu | |
| | | 115 | | | | | 120 | | | | | 125 | | | | |
| CAG | CAG | TCT | GAC | GCT | GAG | TTG | GTG | AAA | CCT | GGG | GCT | TCA | GTG | AAG | ATT | 432 |
| Gln | Gln | Ser | Asp | Ala | Glu | Leu | Val | Lys | Pro | Gly | Ala | Ser | Val | Lys | Ile | |
| | 130 | | | | | 135 | | | | | 140 | | | | | |
| TCC | TGC | AAG | GCT | TCT | GGC | TAC | ACC | TTC | ACT | GAC | CAT | GCA | ATT | CAC | TGG | 480 |
| Ser | Cys | Lys | Ala | Ser | Gly | Tyr | Thr | Phe | Thr | Asp | His | Ala | Ile | His | Trp | |
| 145 | | | | | 150 | | | | | 155 | | | | | 160 | |
| GTG | AAA | CAG | AAC | CCT | GAA | CAG | GGC | CTG | GAA | TGG | ATT | GGA | TAT | TTT | TCT | 528 |
| Val | Lys | Gln | Asn | Pro | Glu | Gln | Gly | Leu | Glu | Trp | Ile | Gly | Tyr | Phe | Ser | |
| | | | | 165 | | | | | 170 | | | | | 175 | | |
| CCC | GGA | AAT | GAT | GAT | TTT | AAA | TAC | AAT | GAG | AGG | TTC | AAG | GGC | AAG | GCC | 576 |
| Pro | Gly | Asn | Asp | Asp | Phe | Lys | Tyr | Asn | Glu | Arg | Phe | Lys | Gly | Lys | Ala | |
| | | | 180 | | | | | 185 | | | | | 190 | | | |
| ACA | CTG | ACT | GCA | GAC | AAA | TCC | TCC | AGC | ACT | GCC | TAC | GTG | CAG | CTC | AAC | 624 |
| Thr | Leu | Thr | Ala | Asp | Lys | Ser | Ser | Ser | Thr | Ala | Tyr | Val | Gln | Leu | Asn | |
| | | 195 | | | | | 200 | | | | | 205 | | | | |
| AGC | CTG | ACA | TCT | GAG | GAT | TCT | GCA | GTG | TAT | TTC | TGT | ACA | AGA | TCC | CTG | 672 |
| Ser | Leu | Thr | Ser | Glu | Asp | Ser | Ala | Val | Tyr | Phe | Cys | Thr | Arg | Ser | Leu | |
| | 210 | | | | | 215 | | | | | 220 | | | | | |
| AAT | ATG | GCC | TAC | TGG | GGT | CAA | GGA | ACC | TCA | GTC | ACC | GTC | TCC | TAATAG | | 720 |
| Asn | Met | Ala | Tyr | Trp | Gly | Gln | Gly | Thr | Ser | Val | Thr | Val | Ser | | | |
| 225 | | | | 230 | | | | | 235 | | | | | | | |

GATCC                                                                                                              725

( 2 ) INFORMATION FOR SEQ ID NO:12:

( i ) SEQUENCE CHARACTERISTICS:
        ( A ) LENGTH: 238 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Asp Val Val Met Thr Gln Thr Pro Leu Ser Leu Pro Val Ser Leu Gly
 1               5                  10                  15
Asp Gln Ala Ser Ile Ser Cys Arg Ser Gln Ser Leu Val His Ser
            20                  25                  30
Asn Gly Asn Thr Tyr Leu Arg Trp Tyr Leu Gln Lys Pro Gly Gln Ser
            35                  40                  45
Pro Lys Val Leu Ile Tyr Lys Val Ser Asn Arg Phe Ser Gly Val Pro
     50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Leu Gly Val Tyr Phe Cys Ser Gln Ser
                85                  90                  95
Thr His Val Pro Trp Thr Phe Gly Gly Gly Thr Lys Leu Glu Ile Lys
            100                 105                 110
Gly Ser Thr Ser Gly Lys Pro Ser Glu Gly Lys Gly Gln Val Gln Leu
         115                 120                 125
Gln Gln Ser Asp Ala Glu Leu Val Lys Pro Gly Ala Ser Val Lys Ile
 130                 135                 140
Ser Cys Lys Ala Ser Gly Tyr Thr Phe Thr Asp His Ala Ile His Trp
145                 150                 155                 160
Val Lys Gln Asn Pro Glu Gln Gly Leu Glu Trp Ile Gly Tyr Phe Ser
                165                 170                 175
Pro Gly Asn Asp Asp Phe Lys Tyr Asn Glu Arg Phe Lys Gly Lys Ala
            180                 185                 190
Thr Leu Thr Ala Asp Lys Ser Ser Thr Ala Tyr Val Gln Leu Asn
            195                 200                 205
Ser Leu Thr Ser Glu Asp Ser Ala Val Tyr Phe Cys Thr Arg Ser Leu
     210                 215                 220
Asn Met Ala Tyr Trp Gly Gln Gly Thr Ser Val Thr Val Ser
225                 230                 235
```

( 2 ) INFORMATION FOR SEQ ID NO:13:

( i ) SEQUENCE CHARACTERISTICS:
        ( A ) LENGTH: 738 base pairs
        ( B ) TYPE: nucleic acid
        ( C ) STRANDEDNESS: both
        ( D ) TOPOLOGY: both ( i x ) FEATURE:
        ( A ) NAME/KEY: CDS
        ( B ) LOCATION: join(1..726)

( x i ) SEQUENCE DESCRIPTION: SEQ ID NO:13:

```
GAC GTC GTG ATG TCA CAG TCT CCA TCC TCC CTA CCT GTG TCA GTT GGC      48
Asp Val Val Met Ser Gln Ser Pro Ser Ser Leu Pro Val Ser Val Gly
 1               5                  10                  15

GAG AAG GTT ACT TTG AGC TGC AAG TCC AGT CAG AGC CTT TTA TAT AGT      96
Glu Lys Val Thr Leu Ser Cys Lys Ser Ser Gln Ser Leu Leu Tyr Ser
            20                  25                  30

GGT AAT CAA AAG AAC TAC TTG GCC TGG TAC CAG CAG AAA CCA GGG CAG     144
Gly Asn Gln Lys Asn Tyr Leu Ala Trp Tyr Gln Gln Lys Pro Gly Gln
            35                  40                  45

TCT CCT AAA CTG CTG ATT TAC TGG GCA TCC GCT AGG GAA TCT GGG GTC     192
Ser Pro Lys Leu Leu Ile Tyr Trp Ala Ser Ala Arg Glu Ser Gly Val
     50                  55                  60

CCT GAT CGC TTC ACA GGC AGT GGA TCT GGG ACA GAT TTC ACT CTC TCC     240
Pro Asp Arg Phe Thr Gly Ser Gly Ser Gly Thr Asp Phe Thr Leu Ser
```

-continued

| | | | | | | | | | | | | | | | | |
|---|---|---|---|---|---|---|---|---|---|---|---|---|---|---|---|---|
| 65 | | | | | 70 | | | | | 75 | | | | | 80 | |
| ATC | AGC | AGT | GTG | AAG | ACT | GAA | GAC | CTG | GCA | GTT | TAT | TAC | TGT | CAG | CAG | 288 |
| Ile | Ser | Ser | Val | Lys | Thr | Glu | Asp | Leu | Ala | Val | Tyr | Tyr | Cys | Gln | Gln | |
| | | | | 85 | | | | | 90 | | | | | 95 | | |
| TAT | TAT | AGC | TAT | CCC | CTC | ACG | TTC | GGT | GCT | GGG | ACC | AAG | CTT | GTG | CTG | 336 |
| Tyr | Tyr | Ser | Tyr | Pro | Leu | Thr | Phe | Gly | Ala | Gly | Thr | Lys | Leu | Val | Leu | |
| | | | 100 | | | | | 105 | | | | | 110 | | | |
| AAA | GGC | TCT | ACT | TCC | GGT | AAA | CCA | TCT | GAA | GGT | AAA | GGT | GAA | GTT | AAA | 384 |
| Lys | Gly | Ser | Thr | Ser | Gly | Lys | Pro | Ser | Glu | Gly | Lys | Gly | Glu | Val | Lys | |
| | | 115 | | | | | 120 | | | | | 125 | | | | |
| CTG | GAT | GAG | ACT | GGA | GGA | GGC | TTG | GTG | CAA | CCT | GGG | AGG | CCC | ATG | AAA | 432 |
| Leu | Asp | Glu | Thr | Gly | Gly | Gly | Leu | Val | Gln | Pro | Gly | Arg | Pro | Met | Lys | |
| | 130 | | | | | 135 | | | | | 140 | | | | | |
| CTC | TCC | TGT | GTT | GCC | TCT | GGA | TTC | ACT | TTT | AGT | GAC | TAC | TGG | ATG | AAC | 480 |
| Leu | Ser | Cys | Val | Ala | Ser | Gly | Phe | Thr | Phe | Ser | Asp | Tyr | Trp | Met | Asn | |
| 145 | | | | | 150 | | | | | 155 | | | | | 160 | |
| TGG | GTC | CGC | CAG | TCT | CCA | GAG | AAA | GGA | CTG | GAG | TGG | GTA | GCA | CAA | ATT | 528 |
| Trp | Val | Arg | Gln | Ser | Pro | Glu | Lys | Gly | Leu | Glu | Trp | Val | Ala | Gln | Ile | |
| | | | | 165 | | | | | 170 | | | | | 175 | | |
| AGA | AAC | AAA | CCT | TAT | AAT | TAT | GAA | ACA | TAT | TAT | TCA | GAT | TCT | GTG | AAA | 576 |
| Arg | Asn | Lys | Pro | Tyr | Asn | Tyr | Glu | Thr | Tyr | Tyr | Ser | Asp | Ser | Val | Lys | |
| | | | 180 | | | | | 185 | | | | | 190 | | | |
| GGC | AGA | TTC | ACC | ATC | TCA | AGA | GAT | GAT | TCC | AAA | AGT | AGT | GTC | TAC | CTG | 624 |
| Gly | Arg | Phe | Thr | Ile | Ser | Arg | Asp | Asp | Ser | Lys | Ser | Ser | Val | Tyr | Leu | |
| | | 195 | | | | | 200 | | | | | 205 | | | | |
| CAA | ATG | AAC | AAC | TTA | AGA | GTT | GAA | GAC | ATG | GGT | ATC | TAT | TAC | TGT | ACG | 672 |
| Gln | Met | Asn | Asn | Leu | Arg | Val | Glu | Asp | Met | Gly | Ile | Tyr | Tyr | Cys | Thr | |
| | 210 | | | | | 215 | | | | | 220 | | | | | |
| GGT | TCT | TAC | TAT | GGT | ATG | GAC | TAC | TGG | GGT | CAA | GGA | ACC | TCA | GTC | ACC | 720 |
| Gly | Ser | Tyr | Tyr | Gly | Met | Asp | Tyr | Trp | Gly | Gln | Gly | Thr | Ser | Val | Thr | |
| 225 | | | | | 230 | | | | | 235 | | | | | 240 | |
| GTC | TCC | TAATAAGGA | TCC | | | | | | | | | | | | | 738 |
| Val | Ser | | | | | | | | | | | | | | | |

(2) INFORMATION FOR SEQ ID NO:14:

(i) SEQUENCE CHARACTERISTICS:
        (A) LENGTH: 242 amino acids
        (B) TYPE: amino acid
        (D) TOPOLOGY: linear (ii) MOLECULE TYPE: protein (xi) SEQUENCE DESCRIPTION: SEQ ID NO:14:

| | | | | | | | | | | | | | | | |
|---|---|---|---|---|---|---|---|---|---|---|---|---|---|---|---|
| Asp | Val | Val | Met | Ser | Gln | Ser | Pro | Ser | Ser | Leu | Pro | Val | Ser | Val | Gly |
| 1 | | | | 5 | | | | | 10 | | | | | 15 | |
| Glu | Lys | Val | Thr | Leu | Ser | Cys | Lys | Ser | Ser | Gln | Ser | Leu | Leu | Tyr | Ser |
| | | | 20 | | | | | 25 | | | | | 30 | | |
| Gly | Asn | Gln | Lys | Asn | Tyr | Leu | Ala | Trp | Tyr | Gln | Gln | Lys | Pro | Gly | Gln |
| | | 35 | | | | | 40 | | | | | 45 | | | |
| Ser | Pro | Lys | Leu | Leu | Ile | Tyr | Trp | Ala | Ser | Ala | Arg | Glu | Ser | Gly | Val |
| | 50 | | | | | 55 | | | | | 60 | | | | |
| Pro | Asp | Arg | Phe | Thr | Gly | Ser | Gly | Ser | Gly | Thr | Asp | Phe | Thr | Leu | Ser |
| 65 | | | | | 70 | | | | | 75 | | | | | 80 |
| Ile | Ser | Ser | Val | Lys | Thr | Glu | Asp | Leu | Ala | Val | Tyr | Tyr | Cys | Gln | Gln |
| | | | | 85 | | | | | 90 | | | | | 95 | |
| Tyr | Tyr | Ser | Tyr | Pro | Leu | Thr | Phe | Gly | Ala | Gly | Thr | Lys | Leu | Val | Leu |
| | | | 100 | | | | | 105 | | | | | 110 | | |
| Lys | Gly | Ser | Thr | Ser | Gly | Lys | Pro | Ser | Glu | Gly | Lys | Gly | Glu | Val | Lys |
| | | 115 | | | | | 120 | | | | | 125 | | | |

```
Leu  Asp  Glu  Thr  Gly  Gly  Gly  Leu  Val  Gln  Pro  Gly  Arg  Pro  Met  Lys
     130                 135                      140

Leu  Ser  Cys  Val  Ala  Ser  Gly  Phe  Thr  Phe  Ser  Asp  Tyr  Trp  Met  Asn
145                      150                      155                      160

Trp  Val  Arg  Gln  Ser  Pro  Glu  Lys  Gly  Leu  Glu  Trp  Val  Ala  Gln  Ile
               165                      170                          175

Arg  Asn  Lys  Pro  Tyr  Asn  Tyr  Glu  Thr  Tyr  Tyr  Ser  Asp  Ser  Val  Lys
               180                      185                     190

Gly  Arg  Phe  Thr  Ile  Ser  Arg  Asp  Asp  Ser  Lys  Ser  Ser  Val  Tyr  Leu
          195                      200                     205

Gln  Met  Asn  Asn  Leu  Arg  Val  Glu  Asp  Met  Gly  Ile  Tyr  Tyr  Cys  Thr
     210                      215                      220

Gly  Ser  Tyr  Tyr  Gly  Met  Asp  Tyr  Trp  Gly  Gln  Gly  Thr  Ser  Val  Thr
225                      230                      235                      240

Val  Ser
```

( 2 ) INFORMATION FOR SEQ ID NO:15:

( i ) SEQUENCE CHARACTERISTICS:
        ( A ) LENGTH: 721 base pairs
        ( B ) TYPE: nucleic acid
        ( C ) STRANDEDNESS: both
        ( D ) TOPOLOGY: both ( i x ) FEATURE:
        ( A ) NAME/KEY: CDS
        ( B ) LOCATION: join(1..711)

( x i ) SEQUENCE DESCRIPTION: SEQ ID NO:15:

```
GAC  GTC  GTG  ATG  ACC  CAG  TCT  CAA  AAA  TTC  ATG  TCC  ACA  TCA  GTA  GGA    48
Asp  Val  Val  Met  Thr  Gln  Ser  Gln  Lys  Phe  Met  Ser  Thr  Ser  Val  Gly
 1                       5                        10                       15

GAC  AGG  GTC  AGC  ATC  ACC  TGC  AAG  GCC  AGT  CAG  AAT  GTT  CGT  ACT  GTT    96
Asp  Arg  Val  Ser  Ile  Thr  Cys  Lys  Ala  Ser  Gln  Asn  Val  Arg  Thr  Val
               20                        25                       30

GTA  GCC  TGG  TAT  CAA  CAG  AAA  CCA  GGG  CAG  TCT  CCT  AAA  ACA  CTG  ATT   144
Val  Ala  Trp  Tyr  Gln  Gln  Lys  Pro  Gly  Gln  Ser  Pro  Lys  Thr  Leu  Ile
          35                        40                       45

TAC  TTG  GCC  TCC  AAC  CGG  CAC  ACT  GGA  GTC  CCT  GAT  CGC  TTC  ACA  GGC   192
Tyr  Leu  Ala  Ser  Asn  Arg  His  Thr  Gly  Val  Pro  Asp  Arg  Phe  Thr  Gly
     50                        55                       60

AGT  GGA  TCT  GGG  ACA  GAT  TTC  ACT  CTC  ACC  ATT  AGC  AAT  GTG  CAA  TCT   240
Ser  Gly  Ser  Gly  Thr  Asp  Phe  Thr  Leu  Thr  Ile  Ser  Asn  Val  Gln  Ser
65                       70                       75                       80

GAA  GAC  CTG  GCA  GAT  TAT  TTC  TGT  CTG  CAA  CAT  TGG  AGT  TAT  CCT  CTC   288
Glu  Asp  Leu  Ala  Asp  Tyr  Phe  Cys  Leu  Gln  His  Trp  Ser  Tyr  Pro  Leu
                    85                        90                       95

ACG  TTC  GGA  TCC  GGG  ACA  AAG  TTG  GAA  GTA  AAA  GGT  TCT  ACC  TCT  GGT   336
Thr  Phe  Gly  Ser  Gly  Thr  Lys  Leu  Glu  Val  Lys  Gly  Ser  Thr  Ser  Gly
               100                      105                      110

TCT  GGT  AAA  TCT  TCT  GAA  GGT  AAA  GGT  GAA  GTG  AAG  CTT  GTG  GAG  TCT   384
Ser  Gly  Lys  Ser  Ser  Glu  Gly  Lys  Gly  Glu  Val  Lys  Leu  Val  Glu  Ser
          115                      120                      125

GGG  GGA  GGC  TTA  GTG  AAG  CCT  GGA  GGG  TCC  CTG  AAA  CTC  TCC  TGT  GCA   432
Gly  Gly  Gly  Leu  Val  Lys  Pro  Gly  Gly  Ser  Leu  Lys  Leu  Ser  Cys  Ala
     130                      135                      140

GCC  TCT  GGA  TTC  GCT  TTC  AGT  ACC  TAT  GAC  ATG  TCT  TGG  GTT  CGC  CAG   480
Ala  Ser  Gly  Phe  Ala  Phe  Ser  Thr  Tyr  Asp  Met  Ser  Trp  Val  Arg  Gln
145                      150                      155                      160

ACT  CCG  GAG  AAG  AGG  CTG  GAG  TGG  GTC  GCA  ACC  ATT  AGT  AGT  GGT  GGT   528
```

```
Thr  Pro  Glu  Lys  Arg  Leu  Glu  Trp  Val  Ala  Thr  Ile  Ser  Ser  Gly  Gly
               165            170                           175

AGT  TAC  ACC  TAC  TAT  TTA  GAC  AGT  GTG  AAG  GGC  CGA  TTC  ACC  ATC  TCC     576
Ser  Tyr  Thr  Tyr  Tyr  Leu  Asp  Ser  Val  Lys  Gly  Arg  Phe  Thr  Ile  Ser
               180                 185                      190

AGA  GAC  AGT  GCC  AGG  AAC  ACC  CTA  TAC  CTG  CAA  ATG  AGC  AGT  CTG  AGG     624
Arg  Asp  Ser  Ala  Arg  Asn  Thr  Leu  Tyr  Leu  Gln  Met  Ser  Ser  Leu  Arg
               195                 200                      205

TCT  GAG  GAC  ACG  GCC  TTG  TAT  TAC  TGT  GCA  CCG  ACT  ACG  GTA  GTC  CCG     672
Ser  Glu  Asp  Thr  Ala  Leu  Tyr  Tyr  Cys  Ala  Pro  Thr  Thr  Val  Val  Pro
     210                           215                      220

TTT  GCT  TAC  TGG  GGC  CAA  GGG  ACT  CTG  GTC  ACT  GTC  TCT  TAATAGATCT        721
Phe  Ala  Tyr  Trp  Gly  Gln  Gly  Thr  Leu  Val  Thr  Val  Ser
225                       230                      235
```

(2) INFORMATION FOR SEQ ID NO:16:

(i) SEQUENCE CHARACTERISTICS:
(A) LENGTH: 237 amino acids
(B) TYPE: amino acid
(D) TOPOLOGY: linear (ii) MOLECULE TYPE: protein (xi) SEQUENCE DESCRIPTION: SEQ ID NO:16:

```
Asp  Val  Val  Met  Thr  Gln  Ser  Gln  Lys  Phe  Met  Ser  Thr  Ser  Val  Gly
1                   5                   10                       15

Asp  Arg  Val  Ser  Ile  Thr  Cys  Lys  Ala  Ser  Gln  Asn  Val  Arg  Thr  Val
               20                  25                       30

Val  Ala  Trp  Tyr  Gln  Gln  Lys  Pro  Gly  Gln  Ser  Pro  Lys  Thr  Leu  Ile
               35                  40                       45

Tyr  Leu  Ala  Ser  Asn  Arg  His  Thr  Gly  Val  Pro  Asp  Arg  Phe  Thr  Gly
     50                       55                  60

Ser  Gly  Ser  Gly  Thr  Asp  Phe  Thr  Leu  Thr  Ile  Ser  Asn  Val  Gln  Ser
65                       70                  75                            80

Glu  Asp  Leu  Ala  Asp  Tyr  Phe  Cys  Leu  Gln  His  Trp  Ser  Tyr  Pro  Leu
                    85                  90                       95

Thr  Phe  Gly  Ser  Gly  Thr  Lys  Leu  Glu  Val  Lys  Gly  Ser  Thr  Ser  Gly
               100                 105                      110

Ser  Gly  Lys  Ser  Ser  Glu  Gly  Lys  Gly  Glu  Val  Lys  Leu  Val  Glu  Ser
          115                 120                      125

Gly  Gly  Gly  Leu  Val  Lys  Pro  Gly  Gly  Ser  Leu  Lys  Leu  Ser  Cys  Ala
     130                      135                      140

Ala  Ser  Gly  Phe  Ala  Phe  Ser  Thr  Tyr  Asp  Met  Ser  Trp  Val  Arg  Gln
145                      150                 155                           160

Thr  Pro  Glu  Lys  Arg  Leu  Glu  Trp  Val  Ala  Thr  Ile  Ser  Ser  Gly  Gly
               165                 170                      175

Ser  Tyr  Thr  Tyr  Tyr  Leu  Asp  Ser  Val  Lys  Gly  Arg  Phe  Thr  Ile  Ser
               180                 185                      190

Arg  Asp  Ser  Ala  Arg  Asn  Thr  Leu  Tyr  Leu  Gln  Met  Ser  Ser  Leu  Arg
               195                 200                      205

Ser  Glu  Asp  Thr  Ala  Leu  Tyr  Tyr  Cys  Ala  Pro  Thr  Thr  Val  Val  Pro
     210                           215                      220

Phe  Ala  Tyr  Trp  Gly  Gln  Gly  Thr  Leu  Val  Thr  Val  Ser
225                       230                      235
```

(2) INFORMATION FOR SEQ ID NO:17:

(i) SEQUENCE CHARACTERISTICS:

(A) LENGTH: 733 base pairs
(B) TYPE: nucleic acid
(C) STRANDEDNESS: both
(D) TOPOLOGY: both (ix) FEATURE:
(A) NAME/KEY: CDS
(B) LOCATION: join(1..723)

(xi) SEQUENCE DESCRIPTION: SEQ ID NO:17:

| | | | | | | | | | | | | | | | | |
|---|---|---|---|---|---|---|---|---|---|---|---|---|---|---|---|---|
| GAC | GTC | GTG | ATG | ACC | CAG | TCT | CAA | AAA | TTC | ATG | TCC | ACA | TCA | GTA | GGA | 48 |
| Asp | Val | Val | Met | Thr | Gln | Ser | Gln | Lys | Phe | Met | Ser | Thr | Ser | Val | Gly | |
| 1 | | | | 5 | | | | | 10 | | | | | 15 | | |
| GAC | AGG | GTC | AGC | ATC | ACC | TGC | AAG | GCC | AGT | CAG | AAT | GTT | CGT | ACT | GTT | 96 |
| Asp | Arg | Val | Ser | Ile | Thr | Cys | Lys | Ala | Ser | Gln | Asn | Val | Arg | Thr | Val | |
| | | | 20 | | | | | 25 | | | | | 30 | | | |
| GTA | GCC | TGG | TAT | CAA | CAG | AAA | CCA | GGG | CAG | TCT | CCT | AAA | ACA | CTG | ATT | 144 |
| Val | Ala | Trp | Tyr | Gln | Gln | Lys | Pro | Gly | Gln | Ser | Pro | Lys | Thr | Leu | Ile | |
| | | | 35 | | | | 40 | | | | | 45 | | | | |
| TAC | TTG | GCC | TCC | AAC | CGG | CAC | ACT | GGA | GTC | CCT | GAT | CGC | TTC | ACA | GGC | 192 |
| Tyr | Leu | Ala | Ser | Asn | Arg | His | Thr | Gly | Val | Pro | Asp | Arg | Phe | Thr | Gly | |
| | | 50 | | | | | 55 | | | | | 60 | | | | |
| AGT | GGA | TCT | GGG | ACA | GAT | TTC | ACT | CTC | ACC | ATT | AGC | AAT | GTG | CAA | TCT | 240 |
| Ser | Gly | Ser | Gly | Thr | Asp | Phe | Thr | Leu | Thr | Ile | Ser | Asn | Val | Gln | Ser | |
| 65 | | | | | 70 | | | | | 75 | | | | | 80 | |
| GAA | GAC | CTG | GCA | GAT | TAT | TTC | TGT | CTG | CAA | CAT | TGG | AGT | TAT | CCT | CTC | 288 |
| Glu | Asp | Leu | Ala | Asp | Tyr | Phe | Cys | Leu | Gln | His | Trp | Ser | Tyr | Pro | Leu | |
| | | | | 85 | | | | | 90 | | | | | 95 | | |
| ACG | TTC | GGA | TCC | GGG | ACA | AAG | TTG | GAA | GTA | AAA | GGT | TCT | ACC | TCT | GGT | 336 |
| Thr | Phe | Gly | Ser | Gly | Thr | Lys | Leu | Glu | Val | Lys | Gly | Ser | Thr | Ser | Gly | |
| | | | 100 | | | | | 105 | | | | | 110 | | | |
| TCT | GGT | AAA | CCC | GGG | AGT | GGT | GAA | GGT | AGC | ACT | AAA | GGT | GAA | GTG | AAG | 384 |
| Ser | Gly | Lys | Pro | Gly | Ser | Gly | Glu | Gly | Ser | Thr | Lys | Gly | Glu | Val | Lys | |
| | | 115 | | | | | 120 | | | | | 125 | | | | |
| CTT | GTG | GAG | TCT | GGG | GGA | GGC | TTA | GTG | AAG | CCT | GGA | GGG | TCC | CTG | AAA | 432 |
| Leu | Val | Glu | Ser | Gly | Gly | Gly | Leu | Val | Lys | Pro | Gly | Gly | Ser | Leu | Lys | |
| | 130 | | | | | 135 | | | | | 140 | | | | | |
| CTC | TCC | TGT | GCA | GCC | TCT | GGA | TTC | GCT | TTC | AGT | ACC | TAT | GAC | ATG | TCT | 480 |
| Leu | Ser | Cys | Ala | Ala | Ser | Gly | Phe | Ala | Phe | Ser | Thr | Tyr | Asp | Met | Ser | |
| 145 | | | | | 150 | | | | | 155 | | | | | 160 | |
| TGG | GTT | CGC | CAG | ACT | CCG | GAG | AAG | AGG | CTG | GAG | TGG | GTC | GCA | ACC | ATT | 528 |
| Trp | Val | Arg | Gln | Thr | Pro | Glu | Lys | Arg | Leu | Glu | Trp | Val | Ala | Thr | Ile | |
| | | | | 165 | | | | | 170 | | | | | 175 | | |
| AGT | AGT | GGT | GGT | AGT | TAC | ACC | TAC | TAT | TTA | GAC | AGT | GTG | AAG | GGC | CGA | 576 |
| Ser | Ser | Gly | Gly | Ser | Tyr | Thr | Tyr | Tyr | Leu | Asp | Ser | Val | Lys | Gly | Arg | |
| | | | 180 | | | | | 185 | | | | | 190 | | | |
| TTC | ACC | ATC | TCC | AGA | GAC | AGT | GCC | AGG | AAC | ACC | CTA | TAC | CTG | CAA | ATG | 624 |
| Phe | Thr | Ile | Ser | Arg | Asp | Ser | Ala | Arg | Asn | Thr | Leu | Tyr | Leu | Gln | Met | |
| | | 195 | | | | | 200 | | | | | 205 | | | | |
| AGC | AGT | CTG | AGG | TCT | GAG | GAC | ACG | GCC | TTG | TAT | TAC | TGT | GCA | CCG | ACT | 672 |
| Ser | Ser | Leu | Arg | Ser | Glu | Asp | Thr | Ala | Leu | Tyr | Tyr | Cys | Ala | Pro | Thr | |
| | 210 | | | | | 215 | | | | | 220 | | | | | |
| ACG | GTA | GTC | CCG | TTT | GCT | TAC | TGG | GGC | CAA | GGG | ACT | CTG | GTC | ACT | GTC | 720 |
| Thr | Val | Val | Pro | Phe | Ala | Tyr | Trp | Gly | Gln | Gly | Thr | Leu | Val | Thr | Val | |
| 225 | | | | | 230 | | | | | 235 | | | | | 240 | |
| TCT | TAATAG | ATCT | | | | | | | | | | | | | | 733 |
| Ser | | | | | | | | | | | | | | | | |

(2) INFORMATION FOR SEQ ID NO:18:

(i) SEQUENCE CHARACTERISTICS:
(A) LENGTH: 241 amino acids
(B) TYPE: amino acid (D) TOPOLOGY: linear (ii) MOLECULE TYPE: protein (xi) SEQUENCE DESCRIPTION: SEQ ID NO:18:

| Asp | Val | Val | Met | Thr | Gln | Ser | Gln | Lys | Phe | Met | Ser | Thr | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Ser | Ile | Thr | Cys | Lys | Ala | Ser | Gln | Asn | Val | Arg | Thr | Val |
|---|---|---|---|---|---|---|---|---|---|---|---|---|---|---|---|
| | | | 20 | | | | 25 | | | | | 30 | | | |

| Val | Ala | Trp | Tyr | Gln | Gln | Lys | Pro | Gly | Gln | Ser | Pro | Lys | Thr | Leu | Ile |
|---|---|---|---|---|---|---|---|---|---|---|---|---|---|---|---|
| | | 35 | | | | | 40 | | | | | 45 | | | |

| Tyr | Leu | Ala | Ser | Asn | Arg | His | Thr | Gly | Val | Pro | Asp | Arg | Phe | Thr | Gly |
|---|---|---|---|---|---|---|---|---|---|---|---|---|---|---|---|
| | 50 | | | | | 55 | | | | | 60 | | | | |

| Ser | Gly | Ser | Gly | Thr | Asp | Phe | Thr | Leu | Thr | Ile | Ser | Asn | Val | Gln | Ser |
|---|---|---|---|---|---|---|---|---|---|---|---|---|---|---|---|
| 65 | | | | | 70 | | | | | 75 | | | | | 80 |

| Glu | Asp | Leu | Ala | Asp | Tyr | Phe | Cys | Leu | Gln | His | Trp | Ser | Tyr | Pro | Leu |
|---|---|---|---|---|---|---|---|---|---|---|---|---|---|---|---|
| | | | | 85 | | | | | 90 | | | | | 95 | |

| Thr | Phe | Gly | Ser | Gly | Thr | Lys | Leu | Glu | Val | Lys | Gly | Ser | Thr | Ser | Gly |
|---|---|---|---|---|---|---|---|---|---|---|---|---|---|---|---|
| | | | 100 | | | | | 105 | | | | 110 | | | |

| Ser | Gly | Lys | Pro | Gly | Ser | Gly | Glu | Gly | Ser | Thr | Lys | Gly | Glu | Val | Lys |
|---|---|---|---|---|---|---|---|---|---|---|---|---|---|---|---|
| | | 115 | | | | 120 | | | | | 125 | | | | |

| Leu | Val | Glu | Ser | Gly | Gly | Gly | Leu | Val | Lys | Pro | Gly | Gly | Ser | Leu | Lys |
|---|---|---|---|---|---|---|---|---|---|---|---|---|---|---|---|
| | 130 | | | | | 135 | | | | | 140 | | | | |

| Leu | Ser | Cys | Ala | Ala | Ser | Gly | Phe | Ala | Phe | Ser | Thr | Tyr | Asp | Met | Ser |
|---|---|---|---|---|---|---|---|---|---|---|---|---|---|---|---|
| 145 | | | | | 150 | | | | | 155 | | | | | 160 |

| Trp | Val | Arg | Gln | Thr | Pro | Glu | Lys | Arg | Leu | Glu | Trp | Val | Ala | Thr | Ile |
|---|---|---|---|---|---|---|---|---|---|---|---|---|---|---|---|
| | | | | 165 | | | | | 170 | | | | | 175 | |

| Ser | Ser | Gly | Gly | Ser | Tyr | Thr | Tyr | Tyr | Leu | Asp | Ser | Val | Lys | Gly | Arg |
|---|---|---|---|---|---|---|---|---|---|---|---|---|---|---|---|
| | | | 180 | | | | | 185 | | | | | 190 | | |

| Phe | Thr | Ile | Ser | Arg | Asp | Ser | Ala | Arg | Asn | Thr | Leu | Tyr | Leu | Gln | Met |
|---|---|---|---|---|---|---|---|---|---|---|---|---|---|---|---|
| | | 195 | | | | | 200 | | | | | 205 | | | |

| Ser | Ser | Leu | Arg | Ser | Glu | Asp | Thr | Ala | Leu | Tyr | Tyr | Cys | Ala | Pro | Thr |
|---|---|---|---|---|---|---|---|---|---|---|---|---|---|---|---|
| | 210 | | | | | 215 | | | | | 220 | | | | |

| Thr | Val | Val | Pro | Phe | Ala | Tyr | Trp | Gly | Gln | Gly | Thr | Leu | Val | Thr | Val |
|---|---|---|---|---|---|---|---|---|---|---|---|---|---|---|---|
| 225 | | | | | 230 | | | | | 235 | | | | | 240 |

Ser (2) INFORMATION FOR SEQ ID NO:19:

(i) SEQUENCE CHARACTERISTICS:
(A) LENGTH: 54 base pairs
(B) TYPE: nucleic acid
(C) STRANDEDNESS: single
(D) TOPOLOGY: both (xi) SEQUENCE DESCRIPTION: SEQ ID NO:19:

TCTGGTTCTG GTAAACCCGG GAGTGGTGAA GGTAGCACTA AAGGTGAAGT GAAG    54

(2) INFORMATION FOR SEQ ID NO:20:

(i) SEQUENCE CHARACTERISTICS:
(A) LENGTH: 30 base pairs
(B) TYPE: nucleic acid
(C) STRANDEDNESS: single
(D) TOPOLOGY: both (xi) SEQUENCE DESCRIPTION: SEQ ID NO:20:

ACCAGAGGTA GAACCTTTTA CTTCCAACTT    30

( 2 ) INFORMATION FOR SEQ ID NO:21:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: both ( x i ) SEQUENCE DESCRIPTION: SEQ ID NO:21:

CAGCTATCGC GATTGC    16

( 2 ) INFORMATION FOR SEQ ID NO:22:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: both ( x i ) SEQUENCE DESCRIPTION: SEQ ID NO:22:

GAGTTCTGAG GTCATTACTG    20

( 2 ) INFORMATION FOR SEQ ID NO:23:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: both ( x i ) SEQUENCE DESCRIPTION: SEQ ID NO:23:

GATTTCACTC TCACCATTAG    20

( 2 ) INFORMATION FOR SEQ ID NO:24:

( i ) SEQUENCE CHARACTERISTICS:
        ( A ) LENGTH: 4 amino acids
        ( B ) TYPE: amino acid
        ( D ) TOPOLOGY: both ( i x ) FEATURE:
        ( A ) NAME/KEY: Peptide
        ( B ) LOCATION: 1
        ( D ) OTHER INFORMATION: /note= "X at position 1 represents
            any amino acid, said amino acid being repeated
            from 0 to 48 times.

( i x ) FEATURE:
        ( A ) NAME/KEY: Peptide
        ( B ) LOCATION: 2
        ( D ) OTHER INFORMATION: /note= "X at position 2 represents
            a charged amino acid. In a preferred embodiment X
            at this position represents lysine or arginine."

( i x ) FEATURE:
        ( A ) NAME/KEY: Peptide
        ( B ) LOCATION: 4
        ( D ) OTHER INFORMATION: /note= "X at position 4 represents
            any amino acid, said amino acid being repeated
            from 0 to 48 times.

( x i ) SEQUENCE DESCRIPTION: SEQ ID NO:24:

Xaa Xaa Pro Xaa
     1

( 2 ) INFORMATION FOR SEQ ID NO:25:

( i ) SEQUENCE CHARACTERISTICS:
        ( A ) LENGTH: 12 amino acids
        ( B ) TYPE: amino acid
        ( D ) TOPOLOGY: both (ix) FEATURE:
    (A) NAME/KEY: Peptide
    (B) LOCATION: 6
    (D) OTHER INFORMATION: /note= "X at position 6 represents
        a charged amino acid. In a preferred embodiment X
        at this position represents lysine or arginine."

(xi) SEQUENCE DESCRIPTION: SEQ ID NO:25:

Gly Ser Thr Ser Gly Xaa Pro Ser Glu Gly Lys Gly
1               5                   10